United States Patent
Cerullo et al.

(10) Patent No.: US 12,337,030 B2
(45) Date of Patent: Jun. 24, 2025

(54) VIRAL VECTOR

(71) Applicant: Valo Therapeutics Oy, Helsinki (FI)

(72) Inventors: Vincenzo Cerullo, Helsinki (FI);
Cristian Capasso, Milan (IT); Sara Feola, Helsinki (FI); Siri Tahtinen, Helsinki (FI)

(73) Assignee: Valo Therapeutics Oy, Helsinki (FI)

( * ) Notice: Subject to any disclaimer, the term of this patent is extended or adjusted under 35 U.S.C. 154(b) by 825 days.

(21) Appl. No.: 17/614,064

(22) PCT Filed: May 21, 2020

(86) PCT No.: PCT/EP2020/064215
§ 371 (c)(1),
(2) Date: Nov. 24, 2021

(87) PCT Pub. No.: WO2020/239609
PCT Pub. Date: Dec. 3, 2020

(65) Prior Publication Data
US 2022/0288184 A1   Sep. 15, 2022

(30) Foreign Application Priority Data

May 24, 2019 (GB) ..................................... 1907413

(51) Int. Cl.
| | |
|---|---|
| A61K 39/12 | (2006.01) |
| A61K 39/00 | (2006.01) |
| A61K 47/00 | (2006.01) |
| A61P 35/00 | (2006.01) |
| C12N 7/00 | (2006.01) |
| C12N 15/00 | (2006.01) |

(52) U.S. Cl.
CPC .......... *A61K 39/12* (2013.01); *A61K 39/0011* (2013.01); *A61K 39/001186* (2018.08); *A61K 39/001188* (2018.08); *A61K 39/001192* (2018.08); *A61K 47/00* (2013.01); *A61P 35/00* (2018.01); *A61K 2039/5256* (2013.01); *A61K 2039/55544* (2013.01); *A61K 2039/572* (2013.01)

(58) Field of Classification Search
None
See application file for complete search history.

(56) References Cited

FOREIGN PATENT DOCUMENTS

| | | |
|---|---|---|
| DE | 100 10 165 A1 | 9/2001 |
| EP | 3 145 537 B1 | 12/2018 |
| WO | WO 2015/177098 A2 | 11/2015 |
| WO | WO 2016/184822 A1 | 11/2016 |
| WO | WO 2019/070991 A1 | 11/2019 |

OTHER PUBLICATIONS

Ylosmaki et al. Personalized Cancer Vaccine Platform for Clinically Relevant Oncolytic Enveloped Viruses. Molecular Therapy vol. 26 No. 9 Sep. 2018, pp. 2315-2325.*
Tahtinen et al. Exploiting Preexisting Immunity to Enhance Oncolytic Cancer Immunotherapy. Cancer Res. Jun. 15, 2020; 80(12): 2575-2585. Epub Feb. 27, 2020.*
Capasso et al., "Oncolytic adenoviruses coated with MHC-I tumor epitopes increase the antitumor immunity and efficacy against melanoma," *OncoImmunology* 5:e1105429, (11 pages), 2015.
International Search Report and Written Opinion mailed on Sep. 8, 2020 in International Application No. PCT/EP2020/064215 (12 pages).
Rice et al., "Critical Components of a DNA Fusion Vaccine Able to Induce Protective Cytotoxic T Cells Against a Single Epitope of a Tumor Antigen," *J Immunol.* 169:3908-3913, 2002.
Search Report mailed on Nov. 22, 2019 in Great Britain Application No. 1907413.7 (5 pages).
Tähtinen et al., "Exploiting Preexisting Immunity to Enhance Oncolytic Cancer Immunotherapy," *Cancer Res.* 80:2575-2585, 2020.
Ylösmaki et al., "Personalized Cancer Vaccine Platform for Clinically Relevant Oncolytic Enveloped Viruses," *Mol Ther.* 26:2315-2325, 2018.

* cited by examiner

*Primary Examiner* — Nianxiang Zou
(74) *Attorney, Agent, or Firm* — Klarquist Sparkman, LLP

(57) ABSTRACT

The invention concerns a novel viral vector with modified viral capsid or viral envelope; a pharmaceutical composition or immunogenic agent or vaccine comprising same; a target cell transformed or transfected with same; a combination therapeutic comprising same; use of same in treatment of cancer, and a method of treating cancer using same.

Figure 1A:
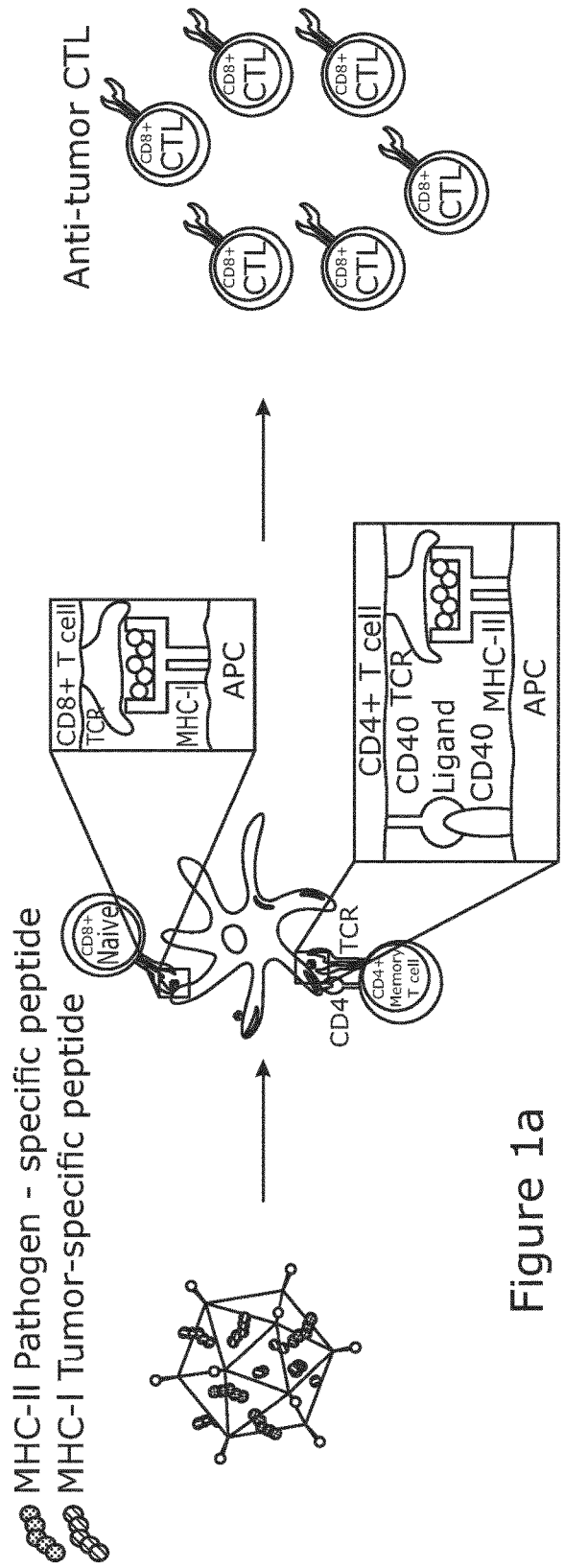

20 Claims, 16 Drawing Sheets
Specification includes a Sequence Listing.

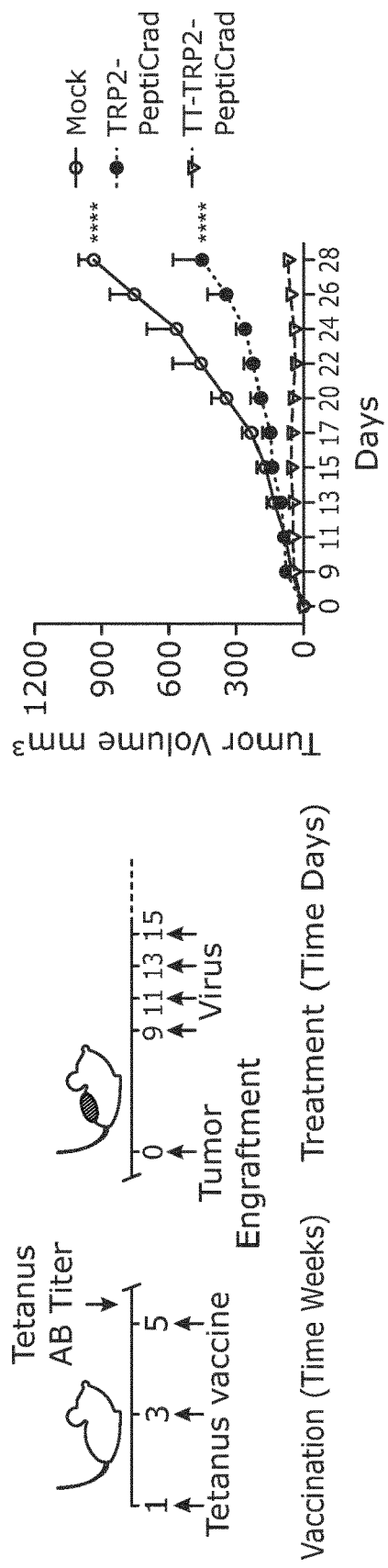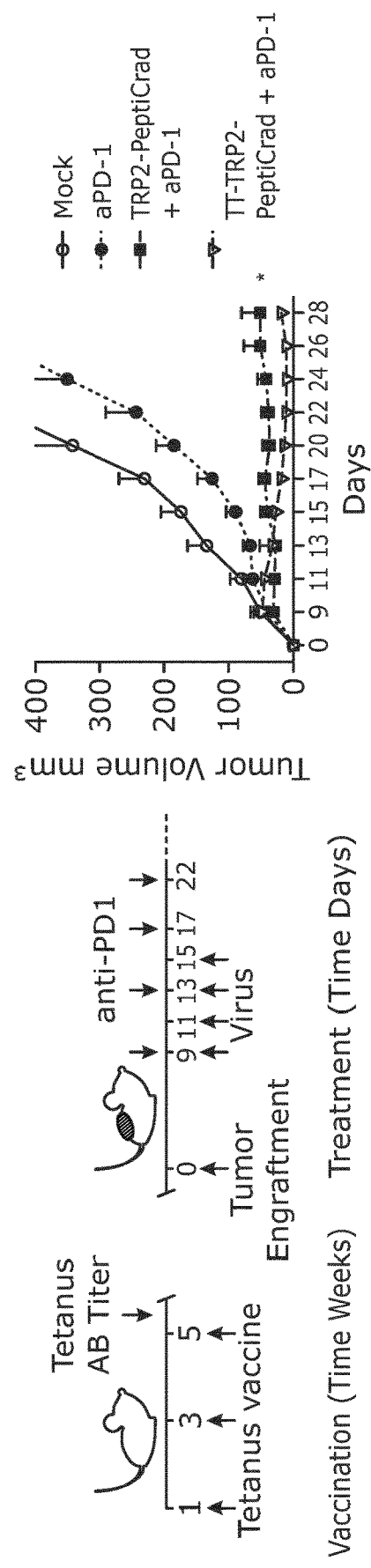
Figure 4A
Figure 4B
Figure 4C
Figure 4D

Spleen dLN dLN dLN

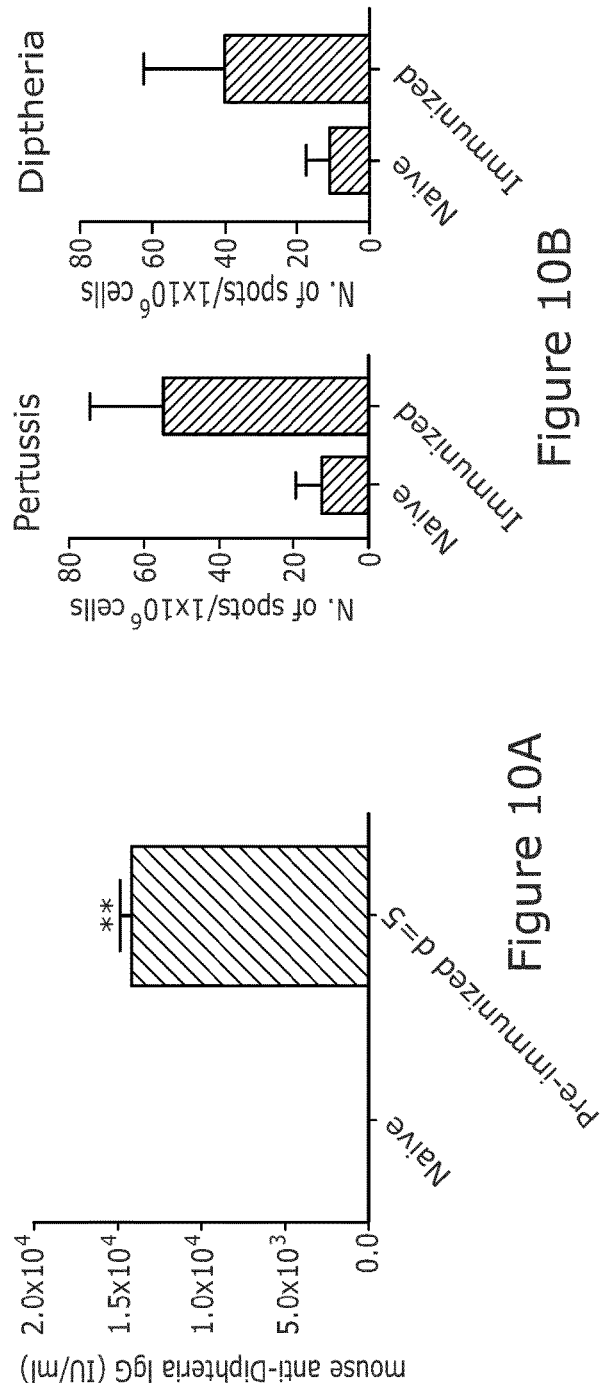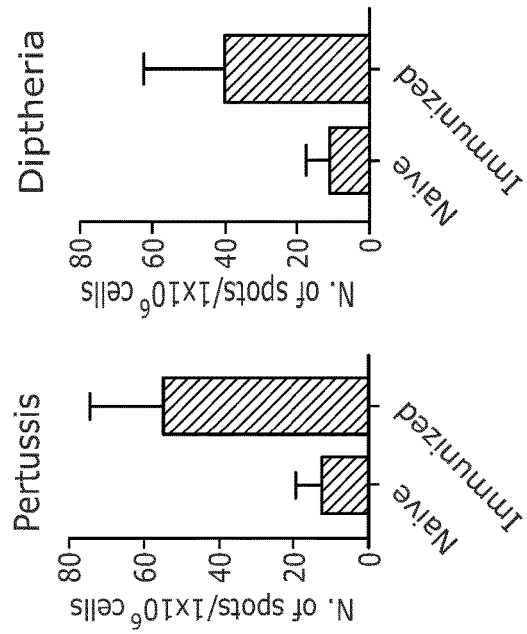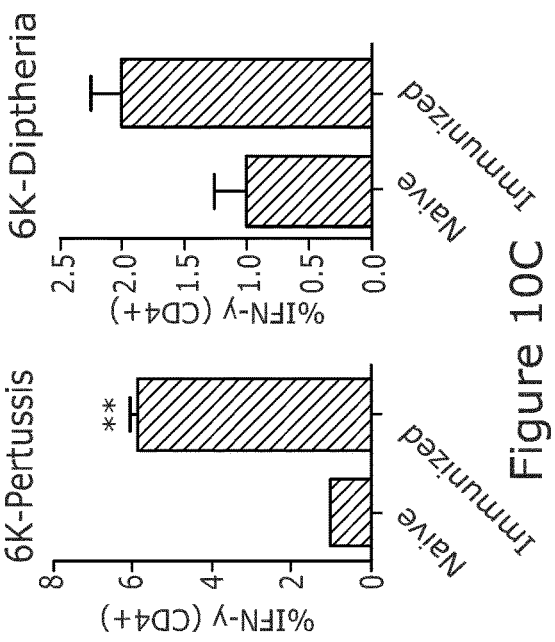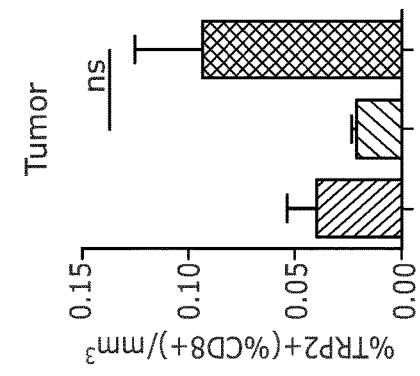
Figure 10A
Figure 10B
Figure 10C
Figure 10D

SEQUENCE LISTING

```
<160> NUMBER OF SEQ ID NOS: 28

<210> SEQ ID NO 1
<211> LENGTH: 15
<212> TYPE: PRT
<213> ORGANISM: Artificial Sequence
<220> FEATURE:
<223> OTHER INFORMATION: tetanus toxin

<400> SEQUENCE: 1

Gln Tyr Ile Lys Ala Asn Ser Lys Phe Ile Gly Ile Thr Glu Leu
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: pertussis

<400> SEQUENCE: 2

Ala Arg Tyr Val Ser Gln Gln Thr Arg Ala Asn Pro Asn Pro Tyr
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: polio mahoney

<400> SEQUENCE: 3

Ile Gln Ser Lys Arg Phe Ala Pro Leu Tyr Ala Val Glu Ala Lys
```

<210> SEQ ID NO 4
<211> LENGTH: 15
<212> TYPE: PRT
<213> ORGANISM: Artificial Sequence
<220> FEATURE:
<223> OTHER INFORMATION: Diptheria

<400> SEQUENCE: 4

Ser Pro Val Tyr Val Gly Asn Gly Val His Ala Asn Leu His Val
1               5                   10                  15

<210> SEQ ID NO 5
<211> LENGTH: 19
<212> TYPE: PRT
<213> ORGANISM: Artificial Sequence
<220> FEATURE:
<223> OTHER INFORMATION: Diptheria

<400> SEQUENCE: 5

Pro Val Phe Ala Gly Ala Asn Tyr Ala Ala Trp Ala Val Asn Val Ala
1               5                   10                  15

Gln Val Ile

<210> SEQ ID NO 6
<211> LENGTH: 15
<212> TYPE: PRT
<213> ORGANISM: Artificial Sequence
<220> FEATURE:
<223> OTHER INFORMATION: Pertussis

<400> SEQUENCE: 6

Ala Arg Tyr Val Ser Gln Gln Thr Arg Ala Asn Pro Asn Pro Tyr
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Polio Mahoney

<400> SEQUENCE: 7

Ile Gln Ser Lys Arg Phe Ala Pro Leu Tyr Ala Val Glu Ala Lys
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Diptheria

<400> SEQUENCE: 8

Ser Pro Val Tyr Val Gly Asn Gly Val His Ala Asn Leu His Val
1               5                   10                  15

<210> SEQ ID NO 9
<211> LENGTH: 9
<212> TYPE: PRT
<213> ORGANISM: Artificial Sequence
<220> FEATURE:
<223> OTHER INFORMATION: gp100 antigen

<400> SEQUENCE: 9

```
Lys Val Pro Arg Asn Gln Asp Trp Leu
1               5
```

```
<210> SEQ ID NO 10
<211> LENGTH: 9
<212> TYPE: PRT
<213> ORGANISM: Artificial Sequence
<220> FEATURE:
<223> OTHER INFORMATION: NY-ESO-1 antigen

<400> SEQUENCE: 10

Ser Leu Leu Met Trp Ile Thr Gln Cys
1               5
```

```
<210> SEQ ID NO 11
<211> LENGTH: 20
<212> TYPE: PRT
<213> ORGANISM: Artificial Sequence
<220> FEATURE:
<223> OTHER INFORMATION: NY-ESO-1 antigen

<400> SEQUENCE: 11

Arg Gly Pro Glu Ser Arg Leu Leu Glu Phe Tyr Leu Ala Met Pro Phe
1               5                   10                  15

Ala Thr Pro Met
            20
```

```
<210> SEQ ID NO 12
<211> LENGTH: 20
<212> TYPE: PRT
<213> ORGANISM: Artificial Sequence
<220> FEATURE:
<223> OTHER INFORMATION: NY-ESO-1 antigen

<400> SEQUENCE: 12

Tyr Leu Ala Met Pro Phe Ala Thr Pro Met Glu Ala Glu Leu Ala Arg
1               5                   10                  15

Arg Ser Leu Ala
            20
```

```
<210> SEQ ID NO 13
<211> LENGTH: 30
<212> TYPE: PRT
<213> ORGANISM: Artificial Sequence
<220> FEATURE:
<223> OTHER INFORMATION: NY-ESO-1 Antigen

<400> SEQUENCE: 13

Arg Gly Pro Glu Ser Arg Leu Leu Glu Phe Tyr Leu Ala Met Pro Phe
1               5                   10                  15

Ala Thr Pro Met Glu Ala Glu Leu Ala Arg Arg Ser Leu Ala
            20                  25                  30
```

```
<210> SEQ ID NO 14
<211> LENGTH: 25
<212> TYPE: PRT
<213> ORGANISM: Artificial Sequence
<220> FEATURE:
<223> OTHER INFORMATION: NY-ESO-1 Antigen

<400> SEQUENCE: 14

Pro Gly Val Leu Leu Lys Glu Phe Thr Val Ser Gly Asn Ile Leu Thr
1               5                   10                  15

Ile Arg Leu Thr Ala Ala Asp His Arg
            20                  25
```

```
<210> SEQ ID NO 15
<211> LENGTH: 20
<212> TYPE: PRT
<213> ORGANISM: Artificial Sequence
<220> FEATURE:
<223> OTHER INFORMATION: NY-ESO-1 Antigen

<400> SEQUENCE: 15

Tyr Leu Ala Met Pro Phe Ala Thr Pro Met Glu Ala Glu Leu Ala Arg
1               5                   10                  15

Arg Ser Leu Ala
            20

<210> SEQ ID NO 16
<211> LENGTH: 22
<212> TYPE: PRT
<213> ORGANISM: Artificial Sequence
<220> FEATURE:
<223> OTHER INFORMATION: NY-ESO-1 Antigen

<400> SEQUENCE: 16

Tyr Leu Ala Met Pro Phe Ala Thr Pro Met Glu Ala Glu Leu Ala Arg
1               5                   10                  15

Arg Ser Leu Ala Glu Glu
            20

<210> SEQ ID NO 17
<211> LENGTH: 20
<212> TYPE: PRT
<213> ORGANISM: Artificial Sequence
<220> FEATURE:
<223> OTHER INFORMATION: MAGE-A3 antigen

<400> SEQUENCE: 17

Val Phe Gly Ile Glu Leu Met Glu Val Asp Pro Ile Gly His Leu Tyr
1               5                   10                  15

Ile Phe Ala Thr
            20

<210> SEQ ID NO 18
<211> LENGTH: 20
<212> TYPE: PRT
<213> ORGANISM: Artificial Sequence
<220> FEATURE:
<223> OTHER INFORMATION: MAGE-A3 antigen

<400> SEQUENCE: 18

Val Phe Gly Ile Glu Leu Met Glu Val Asp Pro Ile Gly His Leu Tyr
1               5                   10                  15

Ile Phe Ala Thr
            20

<210> SEQ ID NO 19
<211> LENGTH: 15
<212> TYPE: PRT
<213> ORGANISM: Artificial Sequence
<220> FEATURE:
<223> OTHER INFORMATION: poly lysine gp100 antigen position 25-35

<400> SEQUENCE: 19

Lys Lys Lys Lys Lys Lys Lys Val Pro Arg Asn Gln Asp Trp Leu
1               5                   10                  15
```

-continued

```
<210> SEQ ID NO 20
<211> LENGTH: 15
<212> TYPE: PRT
<213> ORGANISM: Artificial Sequence
<220> FEATURE:
<223> OTHER INFORMATION: poly lysine NY-ESO-1 antigeb position 157-165

<400> SEQUENCE: 20

Lys Lys Lys Lys Lys Lys Ser Leu Leu Met Trp Ile Thr Gln Cys
1               5                   10                  15

<210> SEQ ID NO 21
<211> LENGTH: 26
<212> TYPE: PRT
<213> ORGANISM: Artificial Sequence
<220> FEATURE:
<223> OTHER INFORMATION: poly lysine NY-ESO-1 antigen position 81-100

<400> SEQUENCE: 21

Lys Lys Lys Lys Lys Lys Arg Gly Pro Glu Ser Arg Leu Leu Glu Phe
1               5                   10                  15

Tyr Leu Ala Met Pro Phe Ala Thr Pro Met
            20                  25

<210> SEQ ID NO 22
<211> LENGTH: 26
<212> TYPE: PRT
<213> ORGANISM: Artificial Sequence
<220> FEATURE:
<223> OTHER INFORMATION: poly lysine NY-ESO-1 antigen position 91-110

<400> SEQUENCE: 22

Lys Lys Lys Lys Lys Lys Tyr Leu Ala Met Pro Phe Ala Thr Pro Met
1               5                   10                  15

Glu Ala Glu Leu Ala Arg Arg Ser Leu Ala
            20                  25

<210> SEQ ID NO 23
<211> LENGTH: 36
<212> TYPE: PRT
<213> ORGANISM: Artificial Sequence
<220> FEATURE:
<223> OTHER INFORMATION: poly lysine NY-ESO-1 antigen position 81-110

<400> SEQUENCE: 23

Lys Lys Lys Lys Lys Lys Arg Gly Pro Glu Ser Arg Leu Leu Glu Phe
1               5                   10                  15

Tyr Leu Ala Met Pro Phe Ala Thr Pro Met Glu Ala Glu Leu Ala Arg
            20                  25                  30

Arg Ser Leu Ala
        35

<210> SEQ ID NO 24
<211> LENGTH: 31
<212> TYPE: PRT
<213> ORGANISM: Artificial Sequence
<220> FEATURE:
<223> OTHER INFORMATION: poly lysine NY-ESO-1 antigen position 119-143

<400> SEQUENCE: 24

Lys Lys Lys Lys Lys Lys Pro Gly Val Leu Leu Lys Glu Phe Thr Val
1               5                   10                  15

Ser Gly Asn Ile Leu Thr Ile Arg Leu Thr Ala Ala Asp His Arg
            20                  25                  30
```

```
<210> SEQ ID NO 25
<211> LENGTH: 29
<212> TYPE: PRT
<213> ORGANISM: Artificial Sequence
<220> FEATURE:
<223> OTHER INFORMATION: poly lysine NY-ESO-1 antigen position 91-110

<400> SEQUENCE: 25

Lys Lys Lys Lys Lys Lys Lys Lys Lys Tyr Leu Ala Met Pro Phe Ala
1               5                   10                  15

Thr Pro Met Glu Ala Glu Leu Ala Arg Arg Ser Leu Ala
            20                  25

<210> SEQ ID NO 26
<211> LENGTH: 28
<212> TYPE: PRT
<213> ORGANISM: Artificial Sequence
<220> FEATURE:
<223> OTHER INFORMATION: poly lysine NY-ESO-1 antigen position 91-110

<400> SEQUENCE: 26

Lys Lys Lys Lys Lys Lys Tyr Leu Ala Met Pro Phe Ala Thr Pro Met
1               5                   10                  15

Glu Ala Glu Leu Ala Arg Arg Ser Leu Ala Glu Glu
            20                  25

<210> SEQ ID NO 27
<211> LENGTH: 26
<212> TYPE: PRT
<213> ORGANISM: Artificial Sequence
<220> FEATURE:
<223> OTHER INFORMATION: poly lysine MAGE-A3 antigen position 161-180

<400> SEQUENCE: 27

Lys Lys Lys Lys Lys Lys Val Phe Gly Ile Glu Leu Met Glu Val Asp
1               5                   10                  15

Pro Ile Gly His Leu Tyr Ile Phe Ala Thr
            20                  25

<210> SEQ ID NO 28
<211> LENGTH: 22
<212> TYPE: PRT
<213> ORGANISM: Artificial Sequence
<220> FEATURE:
<223> OTHER INFORMATION: poly lysine MAGE-A3 antigen position 161-176

<400> SEQUENCE: 28

Lys Lys Lys Lys Lys Lys Val Phe Gly Ile Glu Leu Met Glu Val Asp
1               5                   10                  15

Pro Ile Gly His Leu Tyr
            20
```

VIRAL VECTOR

CROSS REFERENCE TO RELATED APPLICATIONS

This is the U.S. National Stage of International Application No. PCT/EP2020/064215, filed May 21, 2020, which was published in English under PCT Article 21 (2), which in turn claims the benefit of Great Britain Application No. 1907413.7, filed May 24, 2019.

FIELD OF THE INVENTION

The invention concerns a novel viral vector with modified viral capsid or viral envelope; a pharmaceutical composition or immunogenic agent or vaccine comprising same; a target cell transformed or transfected with same; a combination therapeutic comprising same; use of same in treatment of cancer, and a method of treating cancer using same.

BACKGROUND OF THE INVENTION

Prophylactic vaccinations are among the most effective forms of medical interventions with direct clinical and health economic benefits, with the eradication of common deadly infectious diseases being the most obvious example. Most vaccines rely on the use of attenuated pathogens or parts of them and evoke a robust T-cell memory repertoire directed against the pathogen, with CD4+ T cells dominating the memory response. Following immunization, naïve T cells differentiate into T effector memory ($T_{EM}$) cells, that are rapidly re-called when encountering the stimulating antigen, and into T central memory ($T_{CM}$) cells, that are found mainly in lymphoid organs and are not immediately triggered in response to pathogens. A strong repertoire of memory T cells against pathogens that are included in the national vaccine programs exists in the worldwide population.

In contrast, the efficacy of cancer immunotherapy relies on the generation of specific anti-tumor CD8+ T cells that recognize peptides presented by the major histocompatibility complex I (MHC-I). Effective anti-tumor activity requires fast T cell mediated responses. Importantly, it has been shown that the cooperation of CD4+ and CD8+ T cells is required for efficient anti-tumor immunity to occur. Indeed, CD4+ T cells provide signals that improve the functionality of CD8+ T cells within the tumor microenvironment (TME) and their depletion, prior to tumor challenge, has been shown to lead to complete loss of tumor rejection in murine tumor models.

However, although the central role of CD4+ T cells in T cell mediated immunity is well recognized, it has not been elucidated how to optimally utilize the interplay between CD4+ and CD8+ T cell populations in cancer treatment strategies.

There therefore remains a challenge of how to exploit the pathogen-specific T cell memory reservoir, mainly CD4+ T cells, to strengthen the anti-tumor CD8+ CTL response.

To address this, we have used our Peptide-coated Conditionally Replicating Adenovirus (PeptiCRAd) platform, that is based, for example, on an oncolytic adenovirus coated with MHC-specific peptides (11), to evaluate the effect of re-engagement of pathogen-specific CD4+ memory T cells upon anti-tumor CD8+ T cell responses in mice pre-immunized with vaccines specific for human pathogens. Without wishing to be bound to theory, it is believed that antigen presenting cells (APCs) process the virus and tumor- and pathogen-specific peptides, the latter being linked to the viral surface, and present the tumor-specific epitopes to CD8+ T cells and the pathogen-specific epitopes to memory CD4+ T cells, which in turn then sustain the CD8+ T cell-mediated immune response as a bystander effect.

As proof of concept, we used naïve or tetanus-pre-immunized immunocompetent mice engrafted with melanoma (B16.OVA) tumors. Mice were treated with intratumoral injections of PeptiCRAd coated with the antigen SIINFEKL (i.e. a CD8+ T cell epitope of Chicken Ovalbumin) and tetanus toxoid (CD4+ T cell epitope) peptides. As hypothesized, we observed a superior anti-tumor response in mice pre-immunized with the tetanus vaccine and treated with tetanus toxin and melanoma tumor antigen coated viruses (TT-OVA-PeptiCRAd). Interestingly, in naïve mice the superiority of TT-OVA-PeptiCRAd over control treatments was lost, highlighting the prerequisite of the pre-existing immunity against pathogenic antigens in order to exploit the CD4+ T cell memory. We validated this strategy by targeting different pathogens (e.g. Diphtheria and Pertussis), and further in combination with a checkpoint inhibitor treatment (e.g. anti-PD-1 antibody). Engagement of CD4+ T cells by Diphtheria-Pertussis-specific MHC-II-restricted peptides resulted in slower tumor growth in pre-immunized mice. In addition, a more robust effector memory CD4+ T cell infiltration was observed in the Tumor Micro Environment (TME) of treated animals when compared to control animals. These results indicated that the proposed mechanism of action is not restricted to tetanus, but the principle could be applied to other vaccine formulations.

Thus, the proposed viral vector can be used to re-engage a pre-existing CD4+ memory T cell repertoire in order to support and enhance an anti-tumor CD8+ CTL response, paving the way for the next major improvement in cancer immunotherapy.

STATEMENTS OF THE INVENTION

According to a first aspect of the invention there is provided a viral vector having attached to its viral capsid or envelope, polypeptides that have not been genetically encoded by said viral vector but have been attached to the capsid or envelope covalently or non-covalently wherein:
 i) at least one of said polypeptides comprises an antigen from, or of, a pathogen, such as a virus or bacteria, that a subject has been prior immunised against; and
 ii) at least one other of said polypeptides is an anti-tumor or anti-cancer specific polypeptide and so stimulates an anti-tumor or anti-cancer immune response in a subject exposed to said vector.

The "capsid" of the adenovirus or vector refers to the protein shell of the virus. The capsid consists of several oligomeric structural subunits made of proteins called protomers. Further, as will be appreciated by those skilled in the art, certain viruses (e.g. HIV and many animal viruses) have viral "envelopes" covering their protective capsids. The envelopes are typically derived from portions of the host cell membranes (phospholipids and proteins), but include some viral glycoproteins. Accordingly, depending on the nature of the virus, said polypeptides can be attached to the capsid or envelope.

Reference herein to a pathogen most typically includes a virus or bacteria, but it can also include any other pathogen, most suitably one against which an individual has been, or is likely to have been, immunised because, typically, but not exclusively, the pathogen forms part of a vaccination programme, national, international or otherwise.

The present invention concerns re-activation of the pathogen-specific T cell memory reservoir, mainly CD4+ T cells, using antigens of, or from, a pathogen such as a virus or bacteria against which a subject to be treated has been previously immunized, whereby said CD4+ T cells co-operate with cancer-specific CD8+ cytotoxic T-cells in order to enhance the effectiveness of same.

Therefore, in a preferred embodiment of the invention, the antigen according to part i) can be any antigen from, or of, a pathogen, such as a virus or bacteria that a subject has been prior immunised against. Ideally, although not exclusively, the chosen antigen is of, or from, a virus or bacteria that forms part of a widespread and/or routine vaccination programme such as, but not limited to, those selected from the group comprising: Measles morbillivirus, Mumps rupulavirus, Rubella virus, Rotavirus, Varicella zoster virus, Flavivirus (Yellow Fever), Hepatovirus, human papillomavirus, *Streptococcus pneumoniae, Neisseria meningitidis, Corynebacterium diphtheriae, Clostridium tetani, Mycobacterium tuberculosis, Poliovirus, Bordetella pertussis, Vibrio cholerae*, or the like.

In a preferred embodiment only, said polypeptide of part i) is selected form the group comprising:

```
                                        (SEQ ID NO: 1)
QYIKANSKFIGITEL (Tetanus toxin);

(SEQ ID NO: 2)
ARYVSQQTRANPNPY (Pertussis);

(SEQ ID NO: 3)
IQSKRFAPLYAVEAK (Polio Mahoney);

(SEQ ID NO: 4)
SPVYVGNGVHANLHV (Diphtheria);

(SEQ ID NO: 5)
PVFAGANYAAWAVNVAQVI (Diphtheria);

(SEQ ID NO: 6)
ARYVSQQTRANPNPY (Pertussis);

(SEQ ID NO: 7)
IQSKRFAPLYAVEAK (Polio Mahoney);
and (SEQ ID NO: 8)
SPVYVGNGVHANLHV (Diphtheria).
```

Additionally, or alternatively, said polypeptides of part i) include a plurality of polypeptides from, or of, at least one pathogen, such as a virus or bacteria, that a subject has been prior immunised against, in a preferred embodiment said plurality of polypeptides are derived from a number of different pathogens.

In a further preferred embodiment of the invention, the antigen according to part ii) can be any antigen that is an anti-tumor or an anti-cancer antigen and so stimulates an anti-tumor or anti-cancer immune response in a subject exposed to said antigen. Examples of anti-cancer antigens include, but are not limited to: fragments derived from the following peptides: gp100, NY-ESO-1, and Mage-A3, more ideally said antigens include the following fragments:

```
                                        (SEQ ID NO: 9)
KVPRNQDWL (gp100);

(SEQ ID NO: 10)
SLLMWITQC (NY-ESO-1);

(SEQ ID NO: 11)
RGPESRLLEFYLAMPFATPM (NY-ESO-1);

(SEQ ID NO: 12)
YLAMPFATPMEAELARRSLA (NY-ESO-1);

(SEQ ID NO: 13)
RGPESRLLEFYLAMPFATPMEAELARRSLA (NY-ESO-1;

(SEQ ID NO: 14)
PGVLLKEFTVSGNILTIRLTAADHR (NY-ESO-1);

(SEQ ID NO: 15)
YLAMPFATPMEAELARRSLA (NY-ESO-1);

(SEQ ID NO: 16)
YLAMPFATPMEAELARRSLAEE (NY-ESO-1);

(SEQ ID NO: 17)
VFGIELMEVDPIGHLYIFAT (MAGE-A3);
and (SEQ ID NO: 18)
VFGIELMEVDPIGHLY (MAGE-A3).
```

Additionally, or alternatively, said polypeptides of part ii) include a plurality of polypeptides that at least collectively, if not individually, stimulate an anti-tumor or anti-cancer immune response.

Advantageously, said polypeptides stimulate both a pathogen-specific (part i) and a peptide-specific (part ii) immune response in a subject that has already been prior-immunised against said pathogenic antigen. Thus said polypeptides elicit both a CD4+ T cell response and a CD8+ T cell response, the former enhancing the effectiveness of the latter. Moreover, and advantageously, because said polypeptides have not been genetically encoded by said viral vector, but have been attached to the capsid or envelope, covalently or non-covalently, the attachment of said polypeptides to said virus can be executed quickly and efficiently i.e. without having to wait for viral replication in a host cell to take place.

In yet a further preferred embodiment still, said polypeptides are selected from the group comprising: Major Histocompatibility Complex class I (MHC-I)-specific polypeptides, Major Histocompatibility Complex class II (MHC-II)-specific polypeptides and Dendritic Cell (DC) specific polypeptides. Accordingly, said polypeptides can be Major Histocompatibility Complex class I (MHC-I)-specific polypeptides and/or Major Histocompatibility Complex class II (MHC-II)-specific polypeptides and/or Dendritic Cell (DC) specific polypeptides.

Ideally, said viral vector comprises a plurality of MHC-I-specific polypeptides and/or a further plurality of MHC-II-specific polypeptides. Most ideally, the polypeptides according to part i) are MHC-II specific and/the polypeptides according to part ii) are MHC-I specific or visa versa.

In a further preferred embodiment of the invention said polypeptides comprise fusion polypeptides, a part of which comprises an antigen from, or of, a pathogen such as a virus or bacteria that a subject has been prior immunised against; and another part of which is an anti-tumor or anti-cancer specific polypeptide and so stimulates an anti-tumor or anti-cancer immune response in a subject exposed to said vector.

In yet a further preferred embodiment, said polypeptides are polylysine-modified or polyarginine-modified and so comprise a poly-lysine linker or a poly-arginine linker for attaching same to said capsid or envelope. Typically to facilitate attachment said polypeptides are polylysine or polyarginine-extended using at least 4, ideally, 5, 6, 7, 8, or 9 lysines. Most typically 6 lysines are used and attached most preferably, but not exclusively, at the amino end of the polypeptide. More ideally still, said polypeptides have a lysine or arginine tail that includes one other amino acid, preferably for example 5 lysines or arginines, then one proline (or some other single amino acid), and then again 4 more lysines or arginines.

Alternatively, other means known to those skilled in the art are used to attach said polypeptides to the capsid or envelope, such as, but not limited to, the use of a cell penetrating peptide as a linker between the polypeptide and the virus, this is particularly useful for enveloped viruses, and also the use of a cholesterol moiety, electrostatic, disulfide or amide bond linkage may used for either attachment of said polypeptides to the viral capsid or the envelope of the virus.

In a further preferred embodiment, said viral vector is an enveloped or an non-enveloped virus.

As will be appreciated by those skilled in the art, examples of enveloped viruses include families selected from the group comprising: Herpesviruses, Poxviruses, Hepadnaviruses, Flavivirus, Togavirus, Coronavirus, Hepatitis D, Orthomyxovirus, Paramyxovirus, Rhabdovirus, Bunyavirus, Filovirus and Retroviruses.

Alternatively, examples of non-enveloped viruses include families selected from the group comprising: Adenoviruses, Reoviruses, Papillomaviruses, Picornaviruses, Caliciviruses.

In a preferred embodiment, said virus is selected from the group comprising: Herpes Simplex Virus 1 (HSV-1), Herpes Simplex Virus 2 (HSV-2), Vaccinia, Vesicular stomatitis Indiana virus (VSV), Measles Virus (MeV), Maraba virus and New Castle Disease (NDV) virus. Most ideally, said viral vector is Vaccinia virus or HSV-1 or an adenovirus or an oncolytic adenovirus.

As will be appreciated, preferably said viral vector is oncolytic i.e. capable of infecting and killing cancer cells by selective replication in tumour versus normal cells.

The viral vector used in the present invention may also comprise other modifications in addition to those described above. Any additional modifications may optionally be used but are not obligatory for the working of the present invention.

It follows from the above that the viral vector of the invention has been engineered to stimulate an immune response against cancer, specifically, by exploiting the interplay between CD4+ memory T cells and CD8+ T cells and so re-engaging the CD4+ memory effector T cells made against previous (immunised) pathogenic antigens to help fight against cancer with a view to mounting a fast and reliable anti-tumour response. Specifically, it has been found that when APCs/DCs process the virus of the invention and in particular the peptides attached to its surface, the DCs present not only tumor-specific peptides to CD8+ T cells to trigger an anti-tumor immune response but, importantly, they also present pathogen-specific peptides to CD4+ T helper cells that potentiate and sustain the cytotoxic immune response. This highlights the importance of the interplay between the innate and adaptive arm of the immune system as well as the key role of effector memory CD4+ T cells in supporting the ongoing anti-tumor response.

Therefore according to a second aspect of the invention, the invention extends to a pharmaceutical composition or immunogenic agent or vaccine comprising at least one viral vector of the invention and a pharmaceutically acceptable carrier, adjuvant, diluent or excipient.

Suitable pharmaceutical excipients are well known to those of skill in the art. Pharmaceutical compositions may be formulated for administration by any suitable route, for example intratumoral, intramuscular, intra-arterial, intravenous, intrapleural, intravesicular, intracavitary or peritoneal injection, buccal, nasal or bronchial (inhaled), transdermal or parenteral and may be prepared by any methods well known in the art of pharmacy.

The composition may be prepared by bringing into association the above defined viral vector with the carrier. In general, the formulations are prepared by uniformly and intimately bringing into association the viral vector with liquid carriers or finely divided solid carriers or both, and then if necessary shaping the product. The invention extends to methods for preparing a pharmaceutical composition comprising bringing a viral vector as defined herein in conjunction or association with a pharmaceutically or veterinary acceptable carrier or vehicle.

According to a third aspect of the invention, there is provided a target cell transformed or transfected with said viral vector as defined herein.

According to a fourth aspect of the invention, there is provided a combination therapeutic for the treatment of cancer comprising: the viral vector or the pharmaceutical composition or immunogenic agent or vaccine or the cell as defined herein in combination with at least one further therapeutic agent.

Advantageously, it has been found that an anti-tumour effect elicited by the viral vector of the invention is even more prominent when said viral vector is combined with at least one other anti-cancer agent, thus strengthening the rationale behind the use of combined therapies when using viral vector agents. For example, given tumors have evolved several immunosuppressive mechanisms to counteract an immune response against same, the other anti-cancer agent may be a checkpoint inhibitor molecule. The best characterized checkpoint pathways are cytotoxic T-lymphocyte protein 4 (CTLA-4) pathway and programmed cell death protein 1 pathway (PD-1/PD-L1). Thus, the viral vector of the invention can be used in combination with at least one checkpoint modulator such as anti-CTLA-4, anti-PD1, or anti-PD-L1 molecules to counteract the immunosuppressive tumor environment and to cause a strong anti-cancer immune response.

A further at least one other anti-cancer agent includes most suitably cyclophosphamide as it downregulates T-regulatory cells.

However, as will be appreciated by those skilled in the art, said further therapeutic agent can be any anti-cancer agent known in the art.

Additionally, or alternatively still, the invention concerns at least one viral vector or pharmaceutical composition or immunogenic agent or vaccine or cell or combination therapeutic according to the invention for use in the treatment of cancer.

Additionally, or alternatively, the invention concerns the use of at least one viral vector or pharmaceutical composition or immunogenic agent or cell or vaccine or combination therapeutic to treat cancer.

Additionally, or alternatively, the invention concerns the use of at least one viral vector or pharmaceutical composition or immunogenic agent or vaccine or cell or combination therapeutic according to the invention in the manufacture of a medicament to treat cancer.

According to yet a further aspect of the invention, there is therefore provided a method of treating cancer comprising administering an effective amount of at least one viral vector or pharmaceutical composition or immunogenic agent or vaccine or cell or combination therapeutic as described herein to a subject in need thereof.

Reference herein to an "effective amount" of the viral vector or a pharmaceutical composition or immunogenic agent or vaccine comprising same, is one that is sufficient to achieve a desired biological effect, such as cancer cell death. It is understood that the effective dosage will be dependent upon the age, sex, health, and weight of the recipient, kind of concurrent treatment, if any, frequency of treatment, and the nature of the effect desired. Typically, the effective amount is determined by those administering the treatment.

Most preferably the cancer referred to herein includes any one or more of the following cancers: nasopharyngeal cancer, synovial cancer, hepatocellular cancer, renal cancer, cancer of connective tissues, melanoma, lung cancer, bowel cancer, colon cancer, rectal cancer, colorectal cancer, brain cancer, throat cancer, oral cancer, liver cancer, bone cancer, pancreatic cancer, choriocarcinoma, gastrinoma, pheochromocytoma, prolactinoma, T-cell leukemia/lymphoma, neuroma, von Hippel-Lindau disease, Zollinger-Ellison syndrome, adrenal cancer, anal cancer, bile duct cancer, bladder cancer, ureter cancer, oligodendroglioma, neuroblastoma, meningioma, spinal cord tumor, osteochondroma, chondrosarcoma, Ewing's sarcoma, cancer of unknown primary site, carcinoid, carcinoid of gastrointestinal tract, fibrosarcoma, breast cancer, Paget's disease, cervical cancer, esophagus cancer, gall bladder cancer, head cancer, eye cancer, neck cancer, kidney cancer, Wilms' tumor, Kaposi's sarcoma, prostate cancer, testicular cancer, Hodgkin's disease, non-Hodgkin's lymphoma, skin cancer, mesothelioma, multiple myeloma, ovarian cancer, endocrine pancreatic cancer, glucagonoma, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, acoustic neuroma, mycosis fungoides, insulinoma, carcinoid syndrome, somatostatinoma, gum cancer, heart cancer, lip cancer, meninges cancer, mouth cancer, nerve cancer, palate cancer, parotid gland cancer, peritoneum cancer, pharynx cancer, pleural cancer, salivary gland cancer, tongue cancer and tonsil cancer.

In the claims which follow and in the preceding description of the invention, except where the context requires otherwise due to express language or necessary implication, the word "comprise", or variations such as "comprises" or "comprising" is used in an inclusive sense i.e. to specify the presence of the stated features but not to preclude the presence or addition of further features in various embodiments of the invention.

All references, including any patent or patent application, cited in this specification are hereby incorporated by reference. No admission is made that any reference constitutes prior art. Further, no admission is made that any of the prior art constitutes part of the common general knowledge in the art.

Preferred features of each aspect of the invention may be as described in connection with any of the other aspects.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose.

Throughout the description and claims of this specification, the singular encompasses the plural unless the context otherwise requires. In particular, where the indefinite article is used, the specification is to be understood as contemplating plurality as well as singularity, unless the context requires otherwise.

Figures 3A, 3B, 3C:
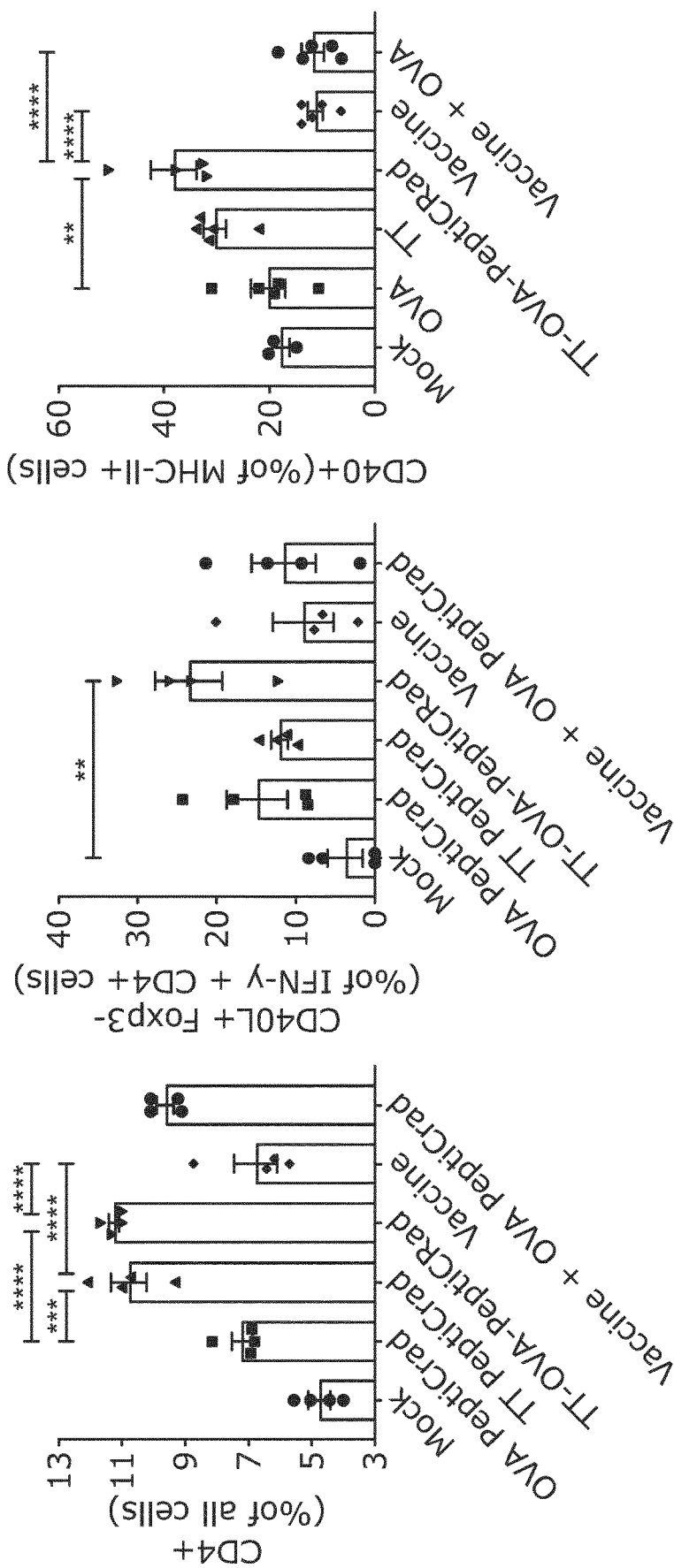

An embodiment of the present invention will now be described by way of example only with reference to the following wherein:

FIGS. 1A-1E. Effect of recalling memory repertoire on murine model of melanoma. (FIG. 1A) A schematic representation of the new hybrid PeptiCRAd system. A single adenovirus is loaded with pathogen-specific peptides to evoke the pre-existing memory T cell repertoire, and with tumor-specific peptides to evoke the anti-tumor T cell repertoire. (FIG. 1B) Treatment scheme. $3 \times 10^5$ B16.OVA cells were injected into the right flank of naïve and tetanus pre-immunized C57BL/6 mice (n=7-8). Treatments were given intra-tumorally 4 times (on days 9, 11, 13 and 15) as indicated in the figure. (FIGS. 1C-1E) The B16.OVA tumor growth was followed until the end of the experiment in naïve and pre-immunized mice. The tumor size is presented as the mean for each treatment±SEM. (Statistical analysis 2way ANOVA, $*p<0.05$, $p<0.005$, $*p<0,001$, $****p<0,0001$);

FIGS. 2A-F Immune cell component within the Tumour Micro Environment (TME) in pre-immunized mice after treatment. Flow cytometry analysis of the tumor samples collected from mice pre-immunized with tetanus at the end of the experiment. The frequency of (FIG. 2A) activated DCs, (FIG. 2B) $CD8^+$ and (FIG. 2C) $CD4^+$ T cells, (FIGS. 2D-2E) and $CD8^+$ and $CD4^+$ effector memory ($CD44^+$ $CD62L^-$) T cells within the TME is reported. The data are plotted as bar graphs and single values. (Statistical analysis Kruskal-Wallis test ANOVA). (FIG. 2F) Flow cytometry analysis of the activation/exhaustion profile of the $CD8^+$ T cells in the tumors. The bar graph depicts gMFI mean of $CD8^+T$ cells that are antigen experienced (PD1+) and exhausted (TIM3+). Significance was assessed by two-tailed unpaired student's t-test, $*p<0.05$, $p<0.005$, $*p<0,001$, $****p<0,0001$;

FIGS. 3A-3C Phenotype of immune cells in lymph-nodes. Lymph-nodes collected from Tetanus Toxin (TT) pre-immunized mice were analysed by flow cytometry to assess the level of (FIG. 3A) TT-specific $CD4^+$, (FIG. 3B) TT-specific $CD4^+$ expressing CD40L and (FIG. 3C) APCs exhibiting CD40 receptor. (Statistical analysis Ordinary One-way ANOVA $*p<0.05$, $p<0.005$, $*p<0,001$, $****p<0,0001$)

Figure 4E:
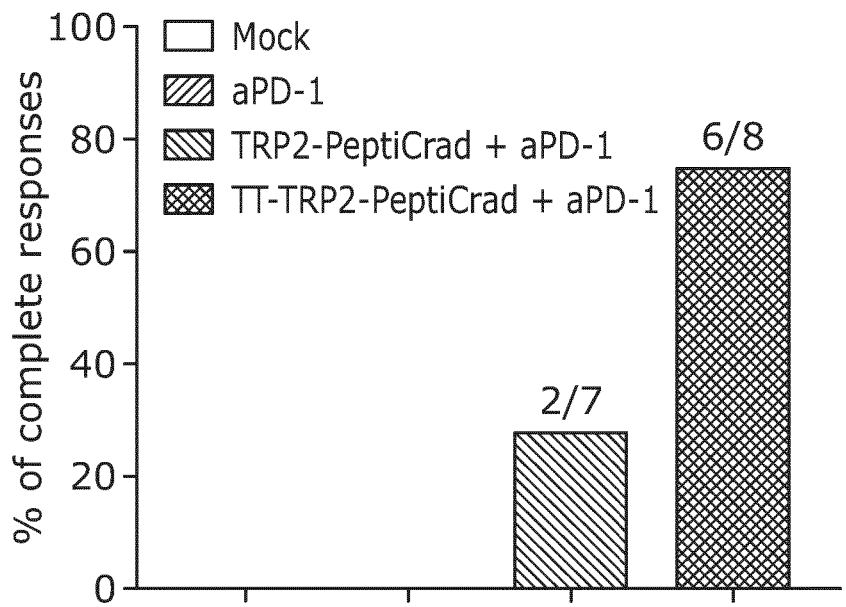
Figure 6A:
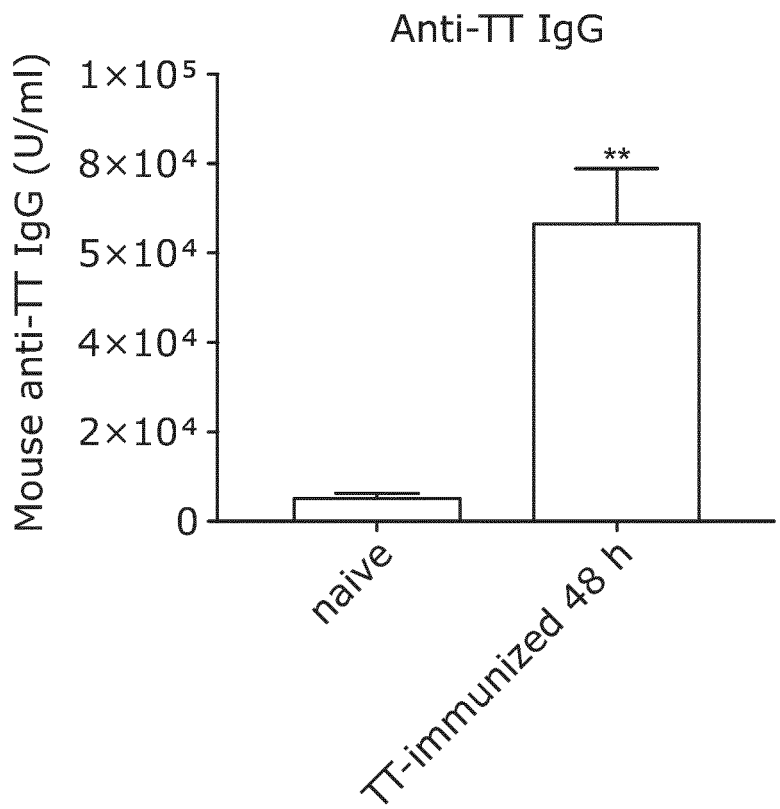
Figure 6B:
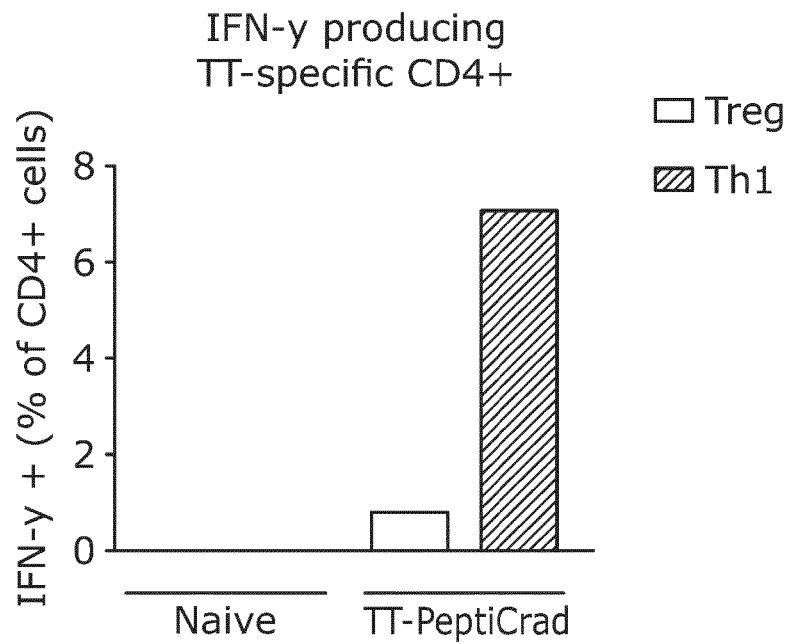
Figure 7A:
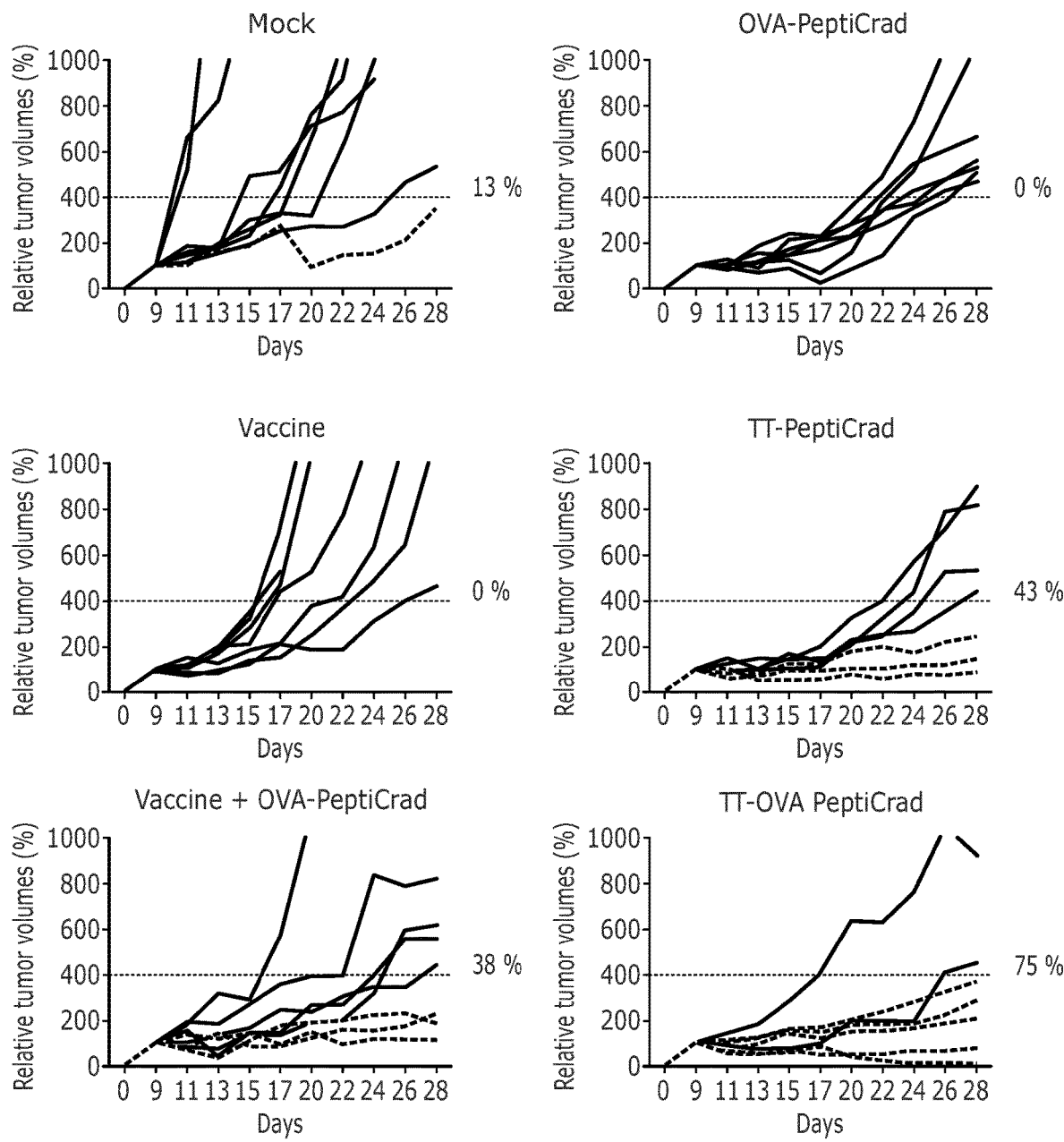
Figure 7B:
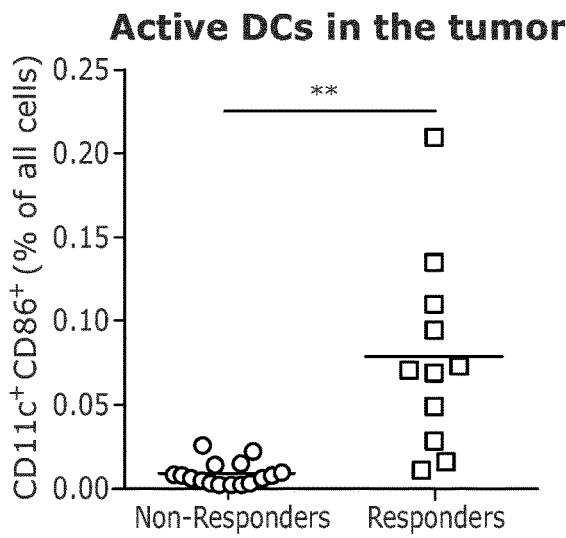
Figure 7C:
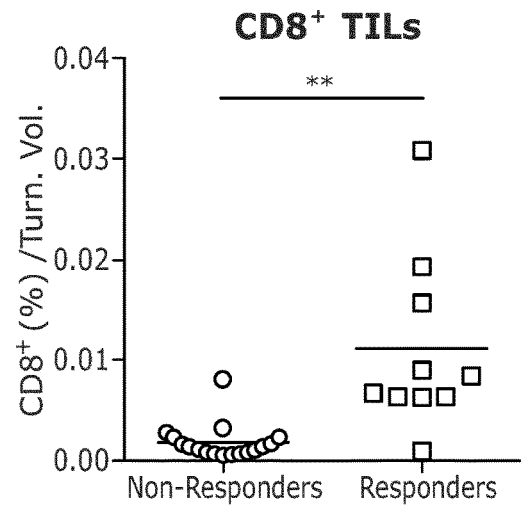
Figure 7D:
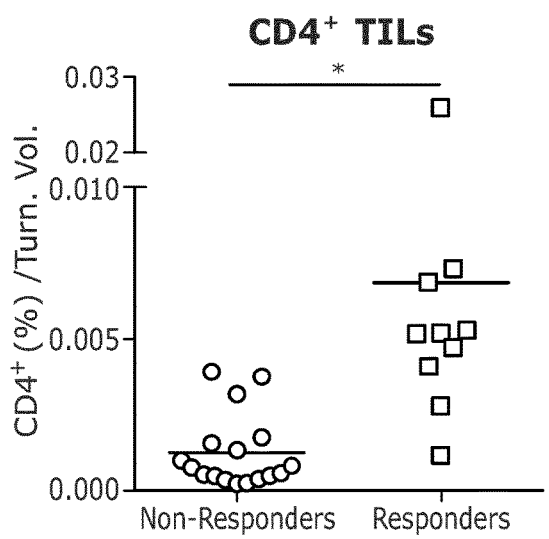
Figure 7E:
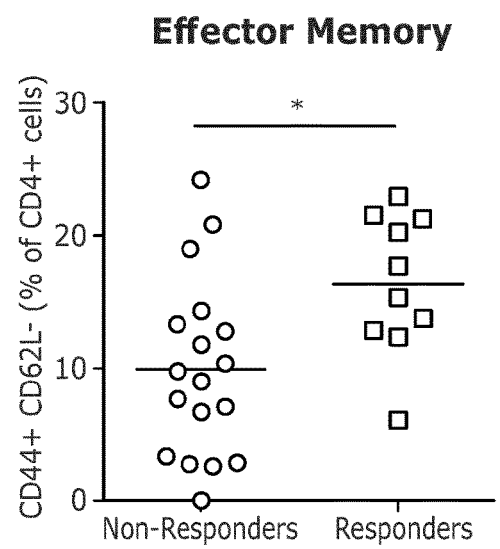
Figure 8A:
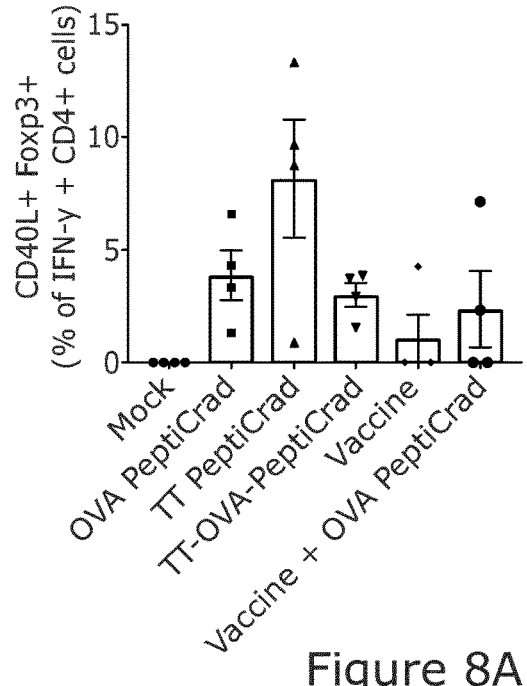
Figure 8B:
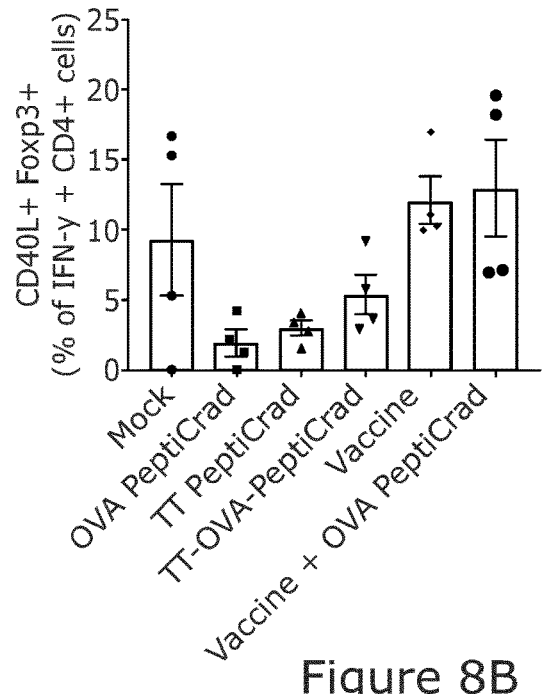
Figure 8C:
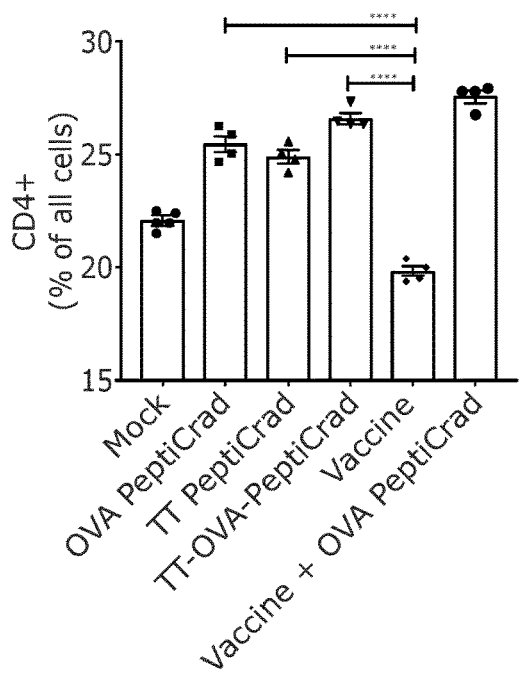
Figure 8D:
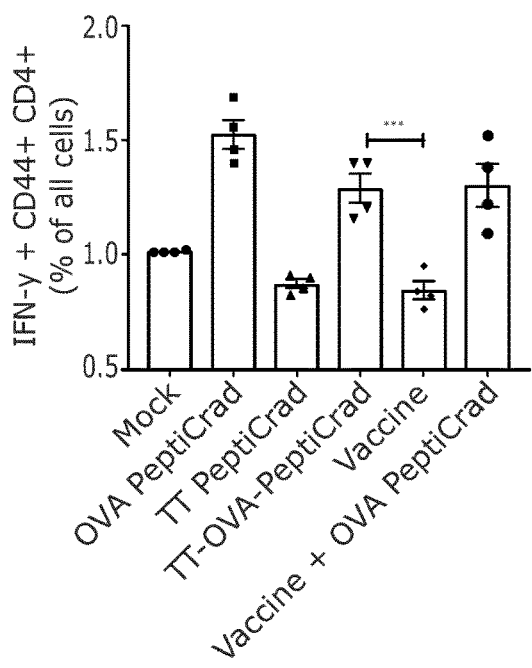
Figure 8E:
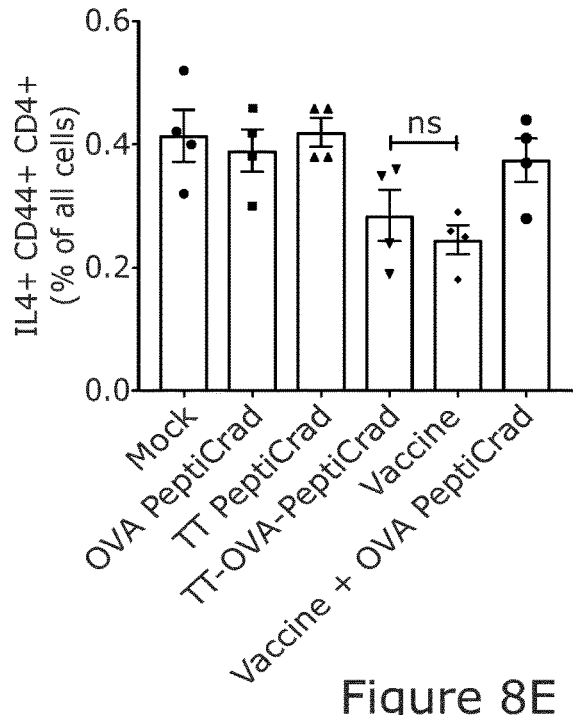
Figure 8F:
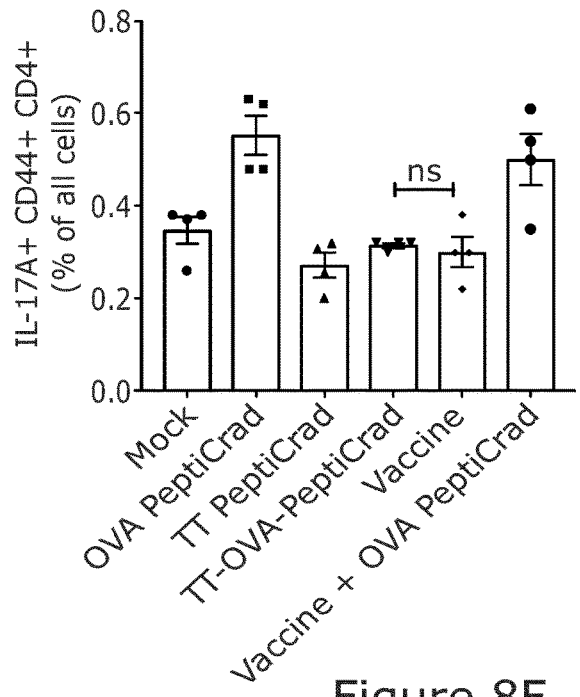
Figure 8G:
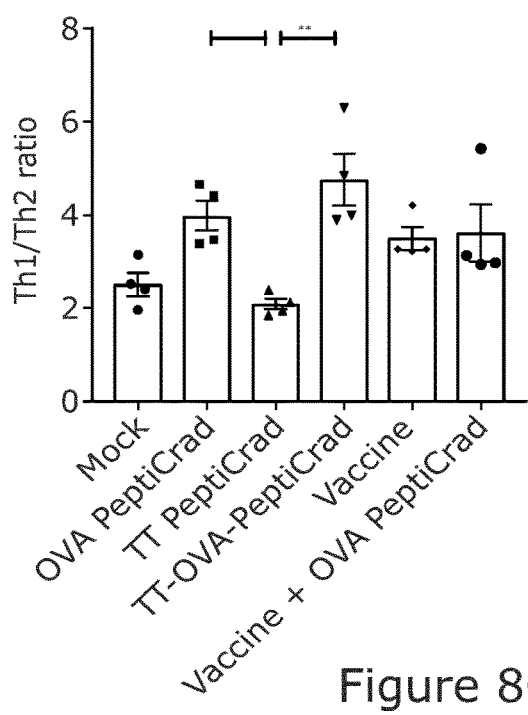
Figure 9A:
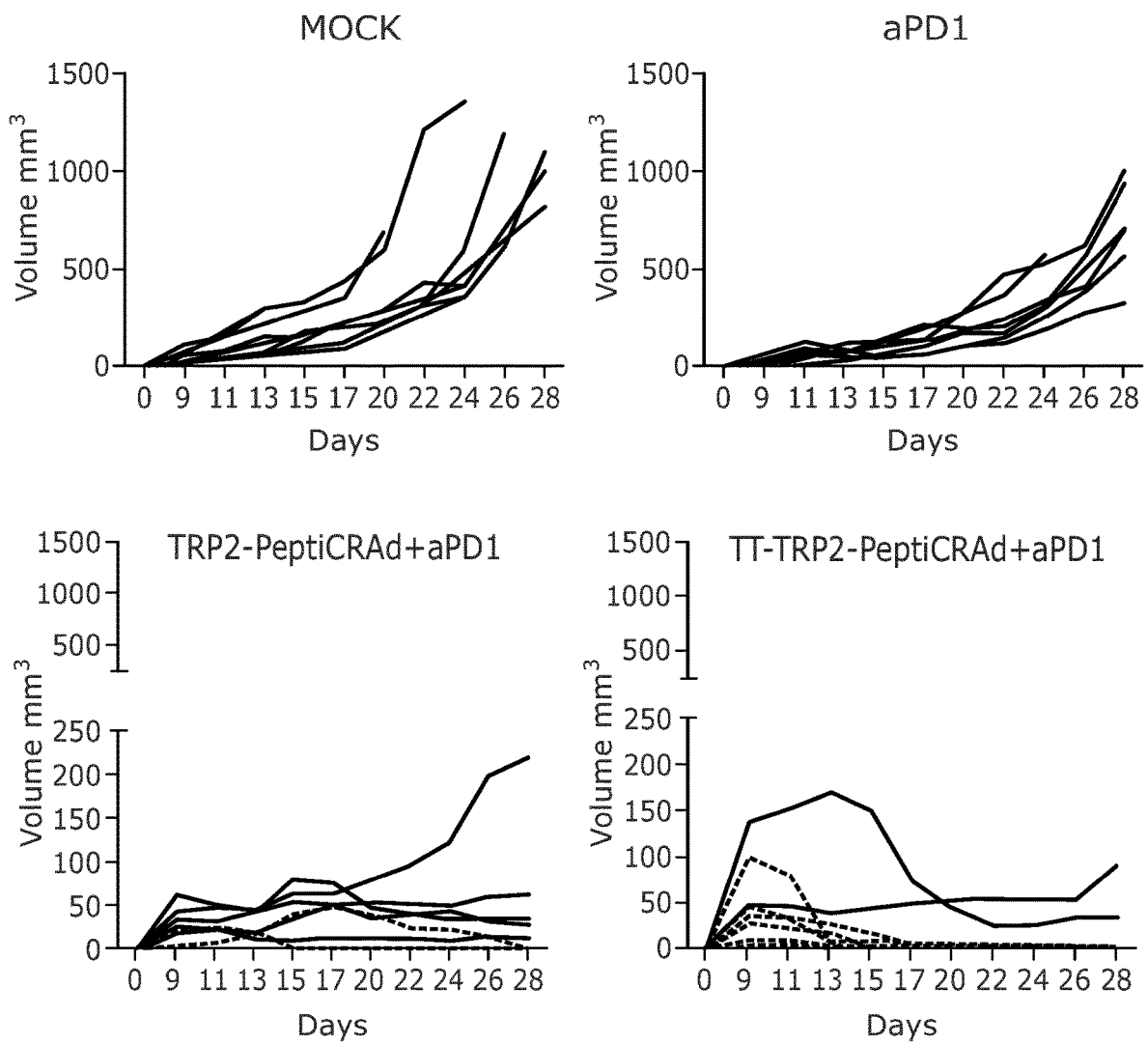
Figure 9B:
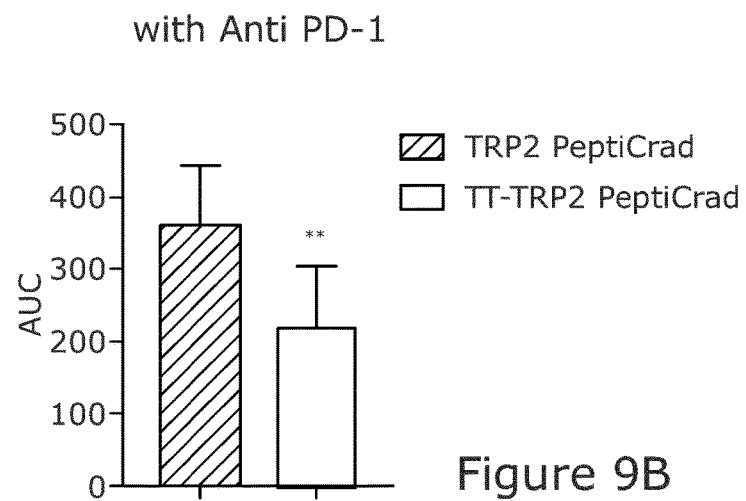

FIGS. 4A-4F Synergistic effect between hybrid PeptiCRAd and aPD1. (FIG. 4A) Treatment scheme. $3 \times 10^5$ B16.OVA cells were injected into the right flank of C57BL/6 mice (n=7-8) pre-immunized with tetanus and the treatments were initiated on established tumors with either the hybrid PeptiCRAd only (FIG. 4A) or a combination with anti-PD-1 antibody (FIG. 4C). The tumor growth curve for mice treated without (FIG. 4B) or with (FIG. 4D) anti-PD-1 is represented as mean±SEM. (FIG. 4E) Complete responses (i.e. the disappearance of the total tumor mass upon treatment) for each group is depicted as the percentage of responders from all treated mice in a single group as well as the ratio of responding individuals to non-responding individuals in a single group. (FIG. 4F) Flow cytometry analysis of CD8+T cells in the tumor from mice treated with tyrosinase related protein 2 (TRP2) TRP2-PeptiCRAd and TT-TRP2-PeptiCRAd. The result is displayed as a single dot for each individual. The control groups that received no peptide vaccine (mock and anti-PD-1 only) are pooled and indicated as "no peptide". Statistical analysis was assessed by 2WAY ANOVA with uncorrected Fisher's LSD (FIG. 4B) and Tukey's multiple comparison test (FIG. 4D);

FIGS. 5A-5D Hybrid PeptiCRAd and aPD1 effects in the context of tetravalent vaccine. (FIG. 5A) $3 \times 10^5$ B16.OVA cells were injected into the right flank of C57BL/6 mice (n=8) pre-immunized with polioboostrix vaccine. Treatments were initiated on established tumors (9 days after tumor implantation) and the mice were treated four times with DP-TRP2-PeptiCRAd (on days 9, 11, 13 and 15) and three times with aPD-1 (on days 9, 13 and 17). (FIG. 5B) The tumor volume is depicted as mean±SEM (statistical analysis 2way ANOVA with Tukey's multiple comparisons test). (FIG. 5C) The level of naïve CD8+ and CD4+ (CD44-CD62L+) T cells in tumor draining lymph nodes of naïve or pre-immunized mice is reported (Statistical analysis unpaired student t-test two tailed, $*p<0.05$, $p<0.005$, $*p<0,001$, $****p<0,0001$). (FIG. 5D) Effector memory (CD44$^+$CD62L$^-$) CD4$^+$ T cells in tumor draining lymph nodes and tumor is shown (Statistical analysis ordinary one-way ANOVA with Tukey's multiple comparison test. $*P \leq 0.05$, $P \leq 0.01$, $*P \leq 0.001$);

FIGS. 6A-6B Detection of humoral and cellular immunity in response to pre-immunization with tetanus vaccine. (FIG. 6A) Detection of anti-tetanus IgG in mouse serum samples. Serum from C57BL/6 naïve mice and mice pre-immunized with tetanus vaccine was collected 48 h after the last boosting and the IgG anti-tetanus titer was measured. The data are shown as mean anti-tetanus IgG U/ml (statistical analysis unpaired student t-test two tailed, $* p<0.05$, $p<0.005$, $*p<0,001$, $****p<0,0001$). (FIG. 6B) Th1 intracellular staining. Splenocytes from untreated naïve and TT-PeptiCRAd treated pre-immunized mice were analysed by flow cytometry to assess the level of IFN-γ (Th1 polarization) and Foxp3 (Tregs) upon TT peptide stimulation;

FIGS. 7A-7E (FIG. 7A) Single tumor growth and immune cell component within the TME. Tumor growth curve for each mouse and one graph for each group are reported with the specific treatment indicated in each graph. Tumor volumes are normalized against the values on the day of the first treatment and presented as mean of percentage±SEM. The percentage displayed next to each graph shows the responders (green), defined as mice with a tumor volume lower than 400% (dashed line). Flow cytometry analysis of DC activation (FIG. 7B) and total CD8+ T cells (FIG. 7C) CD4+ T cells (FIG. 7D) and effector memory (CD44+CD62L−) CD4+T cells (FIG. 7E) within the TME are reported for individual mice in green (responders) and black (non-responders) among each group. The frequency of all the analysed cell types was significantly higher in the responders compared to non-responders. Significance was assessed by two tailed unpaired t-test with Welch's correction for DC activation and for CD8$^+$ and CD4$^+$T cell infiltration analysis, and by two tailed unpaired t-test for the effector memory T cell infiltration;

FIGS. 8A-8G CD40-CD40L crosstalk effects in lymphoid organs. Splenocytes from pre-immunized mice were investigated by flow cytometry for CD4$^+$ T cells expressing (FIG. 8A) or not expressing (FIG. 8B) Foxp3. In draining lymph node total amount of CD4$^+$ T cells is reported (FIG. 8C) and the memory CD4$^+$ T cells (CD44$^+$) were analyzed by intracellular staining for IFN-γ (Th1 phenotype) (FIG. 8D), for IL4 (Th2 phenotype) (FIG. 8E) and for IL-17 (Th17 phenotype) (FIG. 8F). The ratio between Th1 and Th2 polarized CD4$^+$ T cells is depicted in FIG. 8G. Statistical analysis was assessed by ordinary one-way ANOVA with Tukey's multiple comparison test. $*P \leq 0.05$, $P \leq 0.01$, $*P \leq 0.001$;

FIGS. 9A-9B Single tumor growth and area under the curve. (FIG. 9A) Tumor growth curve for each mouse and one graph for each group are reported with the specific treatment indicated in each graph. (FIG. 9B) Area under the curve of the tumor growth is reported as graph bars±SEM for groups treated with anti-PD-1 (Statistical analysis unpaired student t-test two tailed, $*p<0.05$, $p<0.005$, $*p<0,001$, $****p<0,0001$); and FIGS. 10A-10D Immunological characterization in polioboostrix pre-immunized mice. (FIG. 10A) The antibody response induced by PolioBoostrix vaccine. C57BL/6 mice were immunized, and the sera collected after 5 days following the final booster immunization; the anti-diphtheria toxoid antibodies were analysed by ELISA. The data are shown as mean IgG IU/ml±SEM. (FIG. 10B) IFN-γ ELISPOT assay. Splenocytes of naïve mice or mice pre-immunized with PolioBoostrix vaccine were collected one month after the final booster immunization and cultured for 72 h with the stimuli indicated in the figure. The results were expressed as the mean frequency of specific IFN-γ spot-forming cells per $1 \times 10^6$ cells. (statistical analysis unpaired student t-test two tailed, $*p<0.05$, $p<0.005$, $*p<0,001$, $****p<0,0001$). (FIG. 10C) IFN-γ intracellular staining. Splenocytes from naïve and immunized mice were incubated for 6 h with the indicated stimuli and measured by flow cytometry after intracellular staining. (FIG. 10D) The percent of TRP2-specific CD8$^+$ T cells of all CD8$^+$ T cells within the TME. The data were normalized to the tumor volume and plotted as mean±SEM (statistical analysis Kruskal-Wallis test ANOVA).

METHODS AND MATERIALS

Study Design

The main goal of this study is revoking the CD4$^+$ T cell anti-pathogen memory repertoire to boost the anti-tumor response. As proof of principle, our hypothesis was verified in tetanus immunized B16.OVA bearing mice compared to naïve mice. To demonstrate that the use of the memory repertoire gave an advantage over the naïve, the mice's immunological background was examined. Subsequently, we validated our hypothesis using a clinically relevant tumor peptide in combination with an immune checkpoint inhibitor. Lastly, the experiment was repeated with a different type of vaccine, thus verifying the generic use of the underlying principal or conceptual framework. The control and treatments groups are specified in the figure legends. Animal number for each study type was determined by the investigators (each treatment group had not less than n=8 mice). Animals were randomly allocated to the control and the treatment groups.

Cell Lines and Reagents

The cell line B16.OVA, a mouse melanoma cell line expressing chicken ovalbumin (OVA), was cultured according to ATCC recommendations. The cells were cultured in RPMI-1640 with low glucose and supplemented with 10% FBS, 1% antibiotics and 1% L-Glutamine. The cells were cultivated in 37° C., 5% $CO_2$ in a humidified atmosphere.

The following peptides, purchased from Ontores Biotechnologies Co. Ltd (Hangzhou, China), were used throughout the study:

(SEQ ID NO: 1)
KKKKKQYIKANSKFIGITEL (Tetanus toxin);

(SEQ ID NO: 2)
KKKKARYVSQQTRANPNPY (Pertussis);

(SEQ ID NO: 3)
KKKKIQSKRFAPLYAVEAK (Polio Mahoney);

(SEQ ID NO: 4)
KKKKKKSPVYVGNGVHANLHV (Diphtheria);

(SEQ ID NO: 5)
KKKKKKPVFAGANYAAWAVNVAQVI (Diphtheria);

(SEQ ID NO: 6)
ARYVSQQTRANPNPY (Pertussis);

(SEQ ID NO: 7)
IQSKRFAPLYAVEAK (Polio Mahoney);
and (SEQ ID NO: 8)
SPVYVGNGVHANLHV (Diphtheria).

The following peptides are examples of anti-tumour/anti-cancer peptides

| Protein | Sequence | Position (aa) |
|---|---|---|
| gp100 | KKKKKK-KVPRNQDWL (SEQ ID NO: 19) | 25-35 |
| NY-ESO-1 | KKKKKK-SLLMWITQC (SEQ ID NO: 20) | 157-165 (HLA A2) |
| NY-ESO-1 | KKKKKK-RGPESRLLEFYLAMPFATPM (SEQ ID NO: 21) | 81-100 |
| NY-ESO-1 | KKKKKK-YLAMPFATPMEAELARRSLA (SEQ ID NO: 22) | 91-110 |
| NY-ESO-1 | KKKKKK-RGPESRLLEFYLAMPFATPMEAE LARRSLA (SEQ ID NO: 23) | 81-110 |
| NY-ESO-1 | KKKKKK-PGVLLKEFTVSGNILTIRLTAAD HR (SEQ ID NO: 24) | 119-143 |
| NY-ESO-1 | KKKKKKKKK-YLAMPFATPMEAELARRSLA (SEQ ID NO: 25) | 91-110 |
| NY-ESO-1 | KKKKKK-YLAMPFATPMEAELARRSLAEE (SEQ ID NO: 26) | 91-110 |
| MAGE-A3 | KKKKKK-VFGIELMEVDPIGHLYIFAT (SEQ ID NO: 27) | 161-180 |
| MAGE-A3 | KKKKKK-VFGIELMEVDPIGHLY (SEQ ID NO: 28) | 161-176 |

Pre-Immunization of Mice

For tetanus and diphtheria-tetanus-polio-pertussis vaccination, 4-6-week-old female C57BL/6 mice received a primary intramuscular (i.m.) vaccination of Anatetall (GlaxoSmithKline, Italy: 8 IU in 100 μL) or PolioBoostrix (GlaxoSmithKline, Italy: Diphtheria Toxoid 0.4 IU in 100 μL, Tetanus Toxoid 4 IU in 100 μL, *Bordetella pertussis* antigens: Pertussis Toxoid 1.6 mg in 100 μL, Hemagglutinin 1.6 mg in 100 μL and Pertactin 0.5 mg in 100 μL) respectively, administered bilaterally into the quadricep muscle (50 uL per leg). An i.m. booster vaccination (50 μL) was administered twice: a first one 2 weeks after the initial vaccination and a second 2 weeks after the first booster. Mouse IgG antibody responses to tetanus toxoid and diphtheria were measured by ELISA (Xpress Bio Frederik, MD USA). Serum from immunized mice was harvested 5 days after the last immunization and prior to the animal experiment.

Animal Experiments and Ethical Permits

All animal experiments were reviewed and approved by the Experimental Animal Committee of the University of Helsinki and the Provincial Government of Southern Finland (license number ESAVI/9817/04.10.07/2016).

4-6 weeks old female C57BL/6JOIaHsd mice were obtained from Envigo (Laboratory, Bar Harbor, Maine UK). $3\times10^5$ B16.OVA cells were injected subcutaneously into the right flank. Details about the schedule of the treatment can be found in the figure legends. Viral dose was $1\times10^9$ vp/tumor complexed with 20 μg of a single peptide or with 10 μg+10 μg mixture of two peptides. Intratumorally administrated Anatetall vaccine was dosed at 2 IU per mouse. Checkpoint inhibitors were given intraperitoneally at a dose of 100 μg/mouse.

Flow Cytometry

The antibodies used are the following: TruStain Fcblock and anti-CD8-FITC (eBioscience, Affymetrix (Fisher), Foxp3-PE (eBioscience), CD4-PeCy7 (eBioscience), CD3-PerCPCy5.5 (eBioscience), IFNg-APC (eBioscience), CD40L-BV650 (BD Biosciences Bel Art Scienceware (Fisher), IFNg-FITC (BD), IL-17A-PE (BD), CD4-PerCPCy5.5 (BD), IL4-APC (BD), CD44-V450 (BD), CD44-PE (eBioscience), CD4-PeCy7 (eBioscience), CD3-PerCPCy5.5 (eBioscience), CD62L-APC (eBioscience), CCR7-V450 (BD), CD11c-FITC (BD), B220-PE (eBioscience), MHC-II(A-I/E-I)-PeCy7 (eBioscience), CD86-V450 (BD), CD40-APC (eBioscience), CD11b-PerCP-Cy5.5F4/80BV650 (BD), H-2Kb SVYDFFVWL-APC (ProImmune, Oxford Science Park UK), CD8a-FITC (ProImmune). The data were acquired using BDLSRFORTESSA flow cytometer.

Data were analyzed using FlowJo software v9 (Ashland, Oregon, USA).

IFN-γ ELISPOT

IFN-γ ELISPOT assays were performed using a commercially available mouse ELISPOT reagent set (ImmunoSpot, Bonn Germany) and 20 ng/uL of each peptide was tested in in vitro stimulations of splenocytes at 37° C. for 72 h. Spots were counted using an ELISPOT reader system (ImmunoSpot).

PeptiCrad Complex Formation

Oncolytic adenovirus and each epitope with a polyK tail (Ontores, Zhejiang, China) were mixed to prepare the PeptiCRAd complex. We mixed polyK-extended epitopes with Ad-5-D24-CpG for 15 minutes at room temperature prior to treatments with the PeptiCRAd complexes. More details about the stability and formation of the complex can be found in our previous study (11).

Statistical Analysis

Statistical analysis was performed using Graphpad Prism 6.0 software (Graphpad Software Inc., La Jolla, CA USA). For animal experiment, 2 way ANOVA with Tukey's multiple comparisons test was used and $P<0.05$ was considered statistically significant. All results are expressed as the mean±standard error of the mean (SEM).

Details about the statistical tests for each experiment can be found in the corresponding figure legend.

Results and Discussion

Example 1

Pre-Immunization with Tetanus Vaccine Boosts the Antitumor Response of a Double-Coated PeptiCRAd We herein assessed the potential of engaging the CD4+ T cell memory using the PeptiCRAd vaccine platform (11) where we herein coated an oncolytic adenovirus with both MHC-I-restricted tumor-specific peptides and MHC-II-restricted pathogen-specific peptides, and studied the effect on mice tumors in mice pre-immunized for the pathogen (FIG. 1A). Our hypothesis was that by adding the MHC-II-restricted pathogen-specific peptides to the PeptiCRAd platform we would provide a swifter and stronger T helper response, thus enhancing the tumor specific CTL response.

Figure 1B:
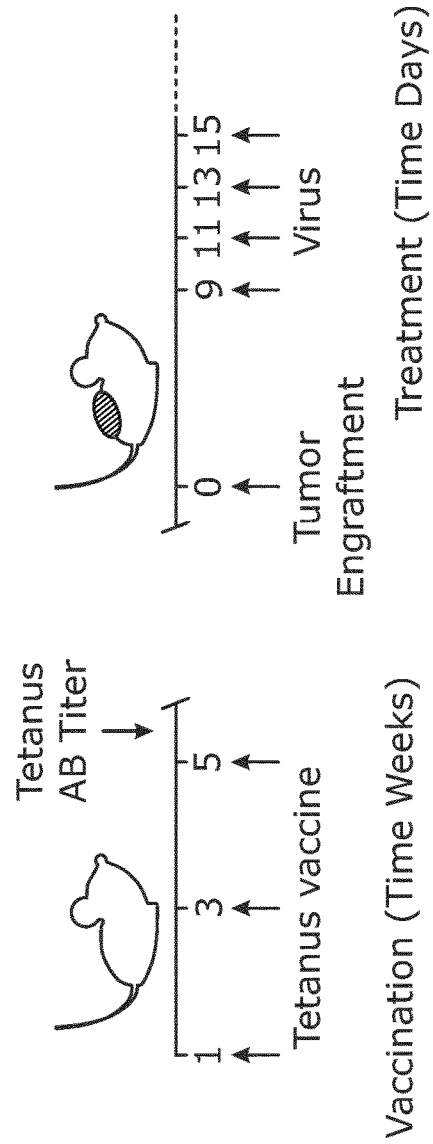
Figure 1C:
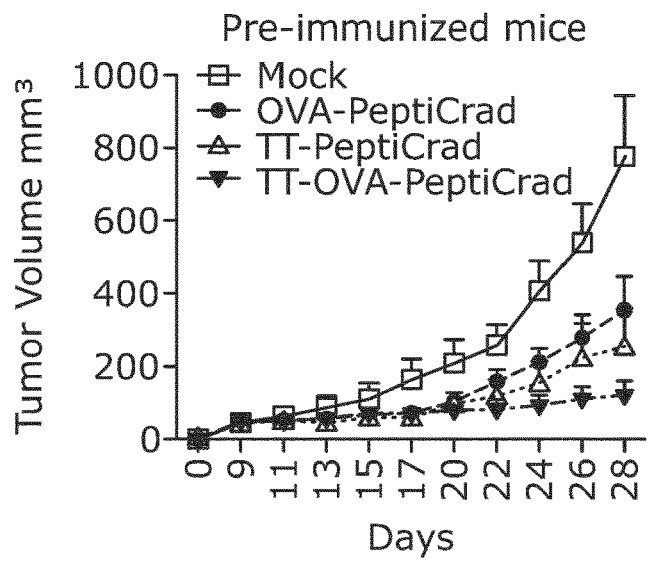

We investigated the anti-tumor effect of modified or double-coated PeptiCRAd in mice pre-immunized with tetanus vaccine intramuscularly and bearing B16.OVA tumors, a melanoma model expressing chicken OVA as a model antigen (15). The OVA-epitope was selected since it has a high immunogenicity and hence provides a suitable model to analyze the generation of T cell response (16). C57BL/6 mice were immunized with tetanus vaccine three times at 2-week intervals (FIG. 1B). 5 weeks after the priming, serum samples were collected from mice and anti-tetanus antibody titer was measured to confirm the success of the vaccination (FIG. 1B and FIG. 6A).

After tumor engraftment, mice were randomized and treated with PeptiCRAd coated with tumor specific peptides (OVA-PeptiCRAd), tetanus-specific peptides (TT-PeptiCRAd) or both tetanus and OVA peptides (TT-OVA-PeptiCRAd). In addition, tetanus vaccine alone or in combination with OVA-PeptiCRAd was used to assess whether intratumorally administrated commercial vaccine can affect tumor growth. All treatments were delivered by intratumoral administration according to the regimen depicted in the FIG. 1B.

Figure 1D:
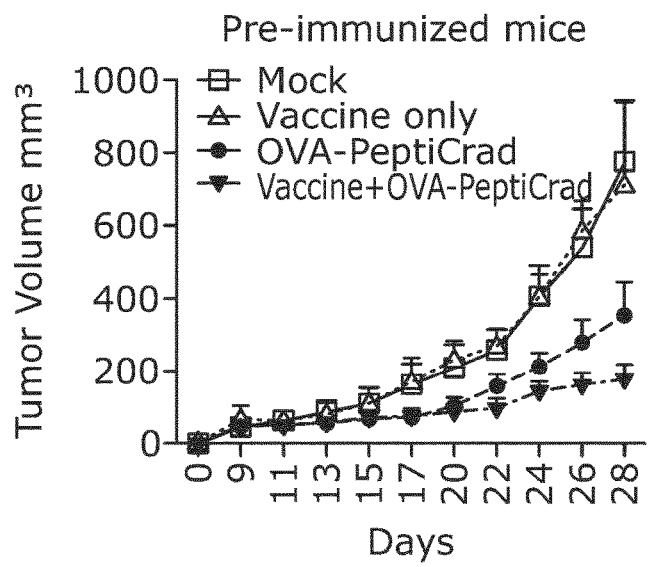

Following therapy, TT-OVA-PeptiCRAd was superior to either one of the single coated viruses in controlling the tumor growth in mice pre-immunized with tetanus toxoid vaccine (FIG. 1C), suggesting that the anti-tetanus memory response indeed enhances the primary immune response elicited against the OVA antigen. The ability of TT-coated PeptiCRAd to elicit mainly Th1-polarized CD4+T cell responses was further corroborated by intracellular staining (FIG. 6B). Less surprisingly, the approach worked also when the tetanus vaccine was re-introduced as a combination with OVA-PeptiCRAd (Vaccine+OVA-PeptiCRAd), whereas tetanus vaccine alone had no therapeutic efficacy (FIG. 1D). Notably, when comparing Vaccine+OVA-PeptiCRAd to OVA-PeptiCRAd, the latter showed a significantly higher anti-tumor efficacy (p=0.05). This suggests that the effect was not caused by the adjuvant contained in the vaccine itself but rather by the presentation of tetanus-specific peptides on MHC-II, engaging CD4+ T cells to help the cytotoxic CD8+ T cell response.

Figure 1E:
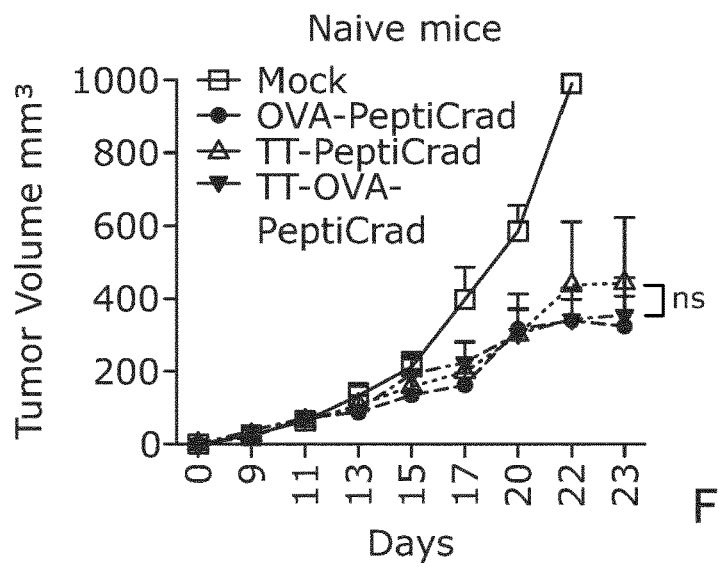

Interestingly, when the same experiment was performed in naïve mice (mice that had not been preimmunized with tetanus vaccine), no statistically significant differences were observed between OVA-PeptiCRAd and TT-OVA-PeptiCRAd. (FIG. 1E).

These results demonstrate that the anti-tumor efficacy of our virus-based PeptiCRAd cancer vaccine is significantly enhanced if it is simultaneously coated also with peptides that are specific for a pathogen for which a pre-existing immunity exists.

Example 2

The Tetanus-Specific Memory Response Favourably Shapes the Immune Environment at the Tumor Site (TME)

In order to gain a deeper understanding of the mode of action of the double-coated PeptiCRAd, we investigated the quality of the immune response elicited by the different treatments. To this end, we analyzed the frequency of different cell populations in the tumor by flow cytometry, most importantly the activated dendritic cells (DC), CD4+ and CD8+ T cells with effector and memory phenotype and experienced and exhausted CD8+ effector T cells.

Figures 2A, 2B, 2C:
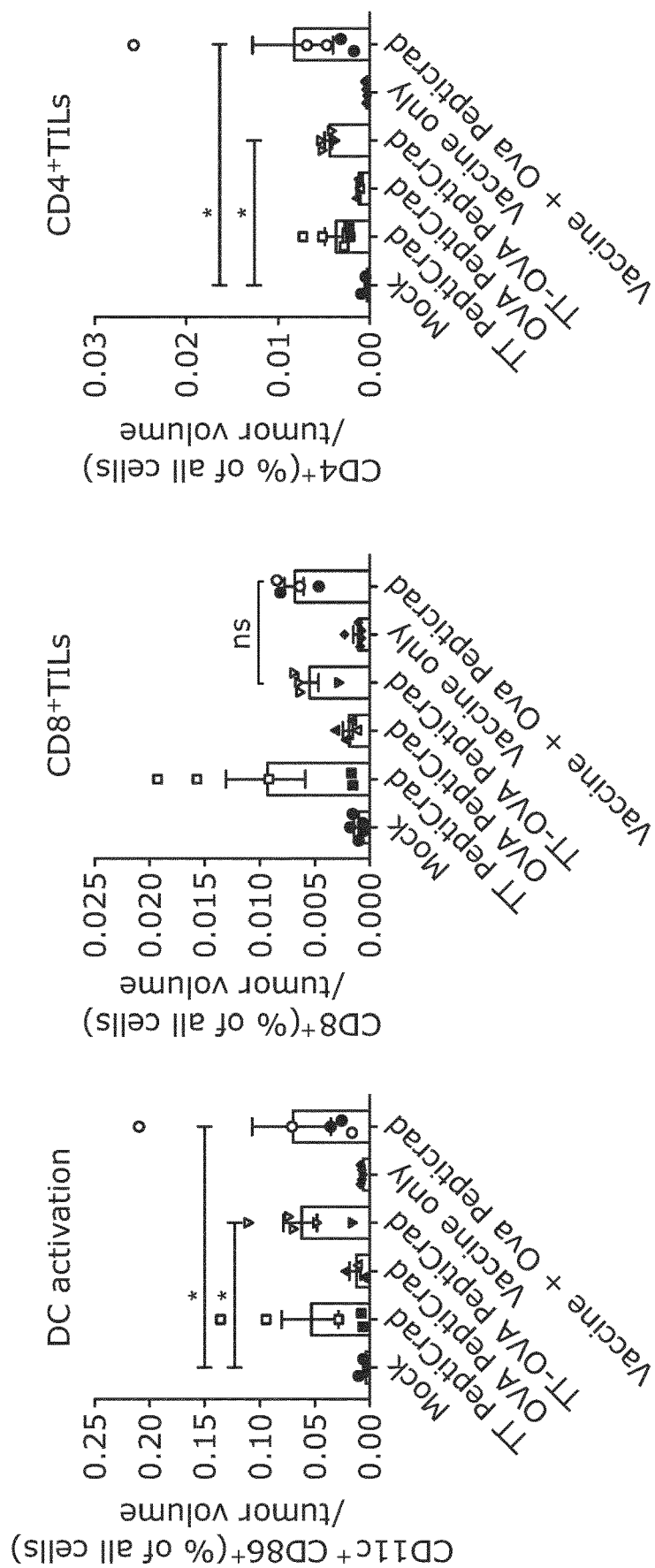
Figures 2D, 2E, 2F:
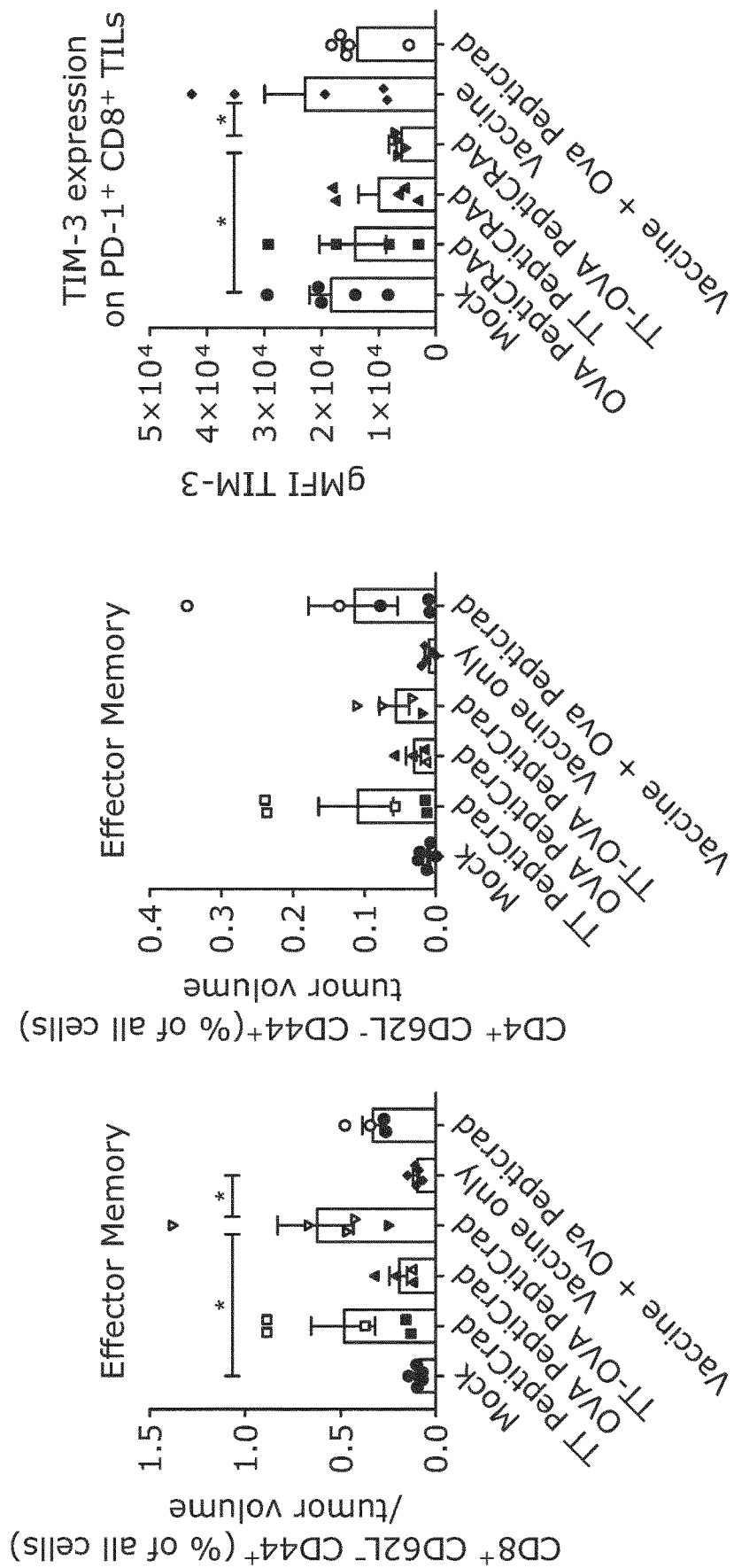

Interestingly, we found an increased frequency of activated intratumoral DCs in all of the groups that had been treated with PeptiCRAd in the context of tetanus antigens (either coated with the TT peptide or co-injected with the whole vaccine) (FIG. 2A). In contrast to these combination treatments, the use of vaccine alone led to poor induction of DC maturation in the TME, suggesting that inclusion of an adenoviral adjuvant may be critical for a proper DC activation in this setting. Moreover, we saw increased levels of CD4+ and CD8+ T cells in the tumors in all groups of mice treated with PeptiCRAd (FIG. 2B-C), which is well in line with what has previously been observed following treatments with virus-based drugs (11). Finally, we wanted to analyze the phenotype of these T cells. Majority of the Tumor-infiltrating lymphocytes (TILs) showed a T effector memory cell phenotype, with an increase in the frequency of CD8+ and CD4+ $T_{EM}$s in groups treated with TT-PeptiCRAd and OVA-TT-PeptiCRAd (FIG. 2D-E). Moreover, the expression level of T-cell immunoglobulin and mucin-domain containing-3 (TIM3) on PD1+ TILs were assessed to study T cell exhaustion. Interestingly, we observed a significantly lower frequency of exhausted CD8+ T cells in the group of mice treated with TT-OVA-PeptiCRAd compared to the other groups, indicating that CD4+T cell help is required for optimal CD8+ T cell activity (FIG. 2F). We concluded that the tetanus pre-existing immunity improved the overall efficacy of the treatment substantially by modifying the immune environment at the tumor site, especially when the treatment was virus based and contained the tetanus vaccine or the tetanus peptides. Of note, the serotype 5 human adenovirus used in these experiments is non-oncolytic in murine tumors, and therefore the effect on tumor control is solely based on anti-tumor immune response. To better elucidate this phenomenon, we re-analyzed all the datasets by stratifying the mice between responders and non-responders and assessed again their immunological responses. As expected, we observed a significant difference between the two groups.

Irrespective of the type of therapy, all responders had an on-going measurable immune response, highlighting the importance of the immune system in controlling the tumour growth, regardless of what kind of treatment they had received. Importantly, the majority of these responders were found in the group of mice treated with TT-OVA-PeptiCRAd (FIG. 7A-E).

Example 3

CD40L Expressing TT-Specific, Th1 Polarized CD4+ T Cells are Detected in Secondary Lymphoid Organs Following TT-OVA-PeptiCRAd Therapy To dissect the possible mechanism of the observed therapeutic efficacy, we assessed levels and phenotype of immune cells in secondary lymphoid organs of pre-immunized mice. As expected, PeptiCRAd treated mice showed expansion of CD4+ T cell compartment both in the spleen and in the draining lymph nodes (FIG. 3A and FIG. 8C). More importantly, a significant increase of TT-specific CD4+ T cells expressing CD40 ligand (CD40L) was observed in TT-OVA treated mice (FIG. 3B). The majority of these CD40L+ cells were polarized towards Th1 phenotype, albeit some TT-specific Foxp3+ T regulatory cells (Tregs) were also detected (FIG. 8A-B). Analysis of dLNs revealed that the intratumoral vaccination with TT-OVA-PeptiCRAd induced mainly IFN-gamma producing Th1 memory cells at the expense of IL-4 secreting Th2 cells, whereas no differences was observed in IL-17A producing Th17 cells (FIG. 8D-G). Since CD4+ T cell-associated CD40L has been shown to be important in stimulating cytotoxic CD8+ T cell responses, we wanted to study whether we can see CD40+ antigen presenting cells. Indeed, when pre-immunized mice were intratumorally treated with TT-OVA-PeptiCRAd, a significantly higher frequency of CD40+ expressing APCs was detected (FIG. 3C), further suggesting that double-coated PeptiCRAd stimulates TT-specific CD4+ memory T cells, that in turn could license professional APCs via CD40-CD40L interaction.

Example 4

Combination with Immune Checkpoint Inhibitors Increases the Number of Responders and Leads to Complete Tumor Rejection We have previously shown that a combination of tumor-targeted PeptiCRAd with immune checkpoint inhibitors is synergistic in terms of improved anti-tumor efficacy (8). Thus, we wanted to assess whether the vaccine-induced pre-existing immunity would further enhance this synergy, particularly by increasing the frequency of mice responding to the therapy.

In order to test this hypothesis, we coated the virus with TT and tyrosinase related protein 2 (TRP2) peptides (TRP2180-188 (23)), which is naturally occurring melanoma-associated antigen and hence more clinically relevant epitope than OVA. Tetanus toxoid pre-immunized mice were implanted with subcutaneous tumors and treated intratumorally with a PeptiCRAd coated with TRP2 peptides only (TRP2-PeptiCRAd) or with a PeptiCRAd coated with both TRP2 and TT peptides (TT-TRP2-PeptiCRAd) (FIG. 4A). Similarly, as in FIG. 1, we observed a significant inhibition of tumor growth in mice treated with the double-coated virus compared to controls (FIG. 4B).

Interestingly, when we combined the PeptiCRAd treatments with a PD-1 blocking monoclonal antibody, we observed a significant increase in efficacy of both TRP2-PeptiCRAd and TT-TRP2-PeptiCRAd treatments (FIG. 4C-D). However, the double-coated PeptiCRAd was still more effective than the virus coated with a single peptide in terms of tumor growth control (FIG. 9B).

Figure 4F:
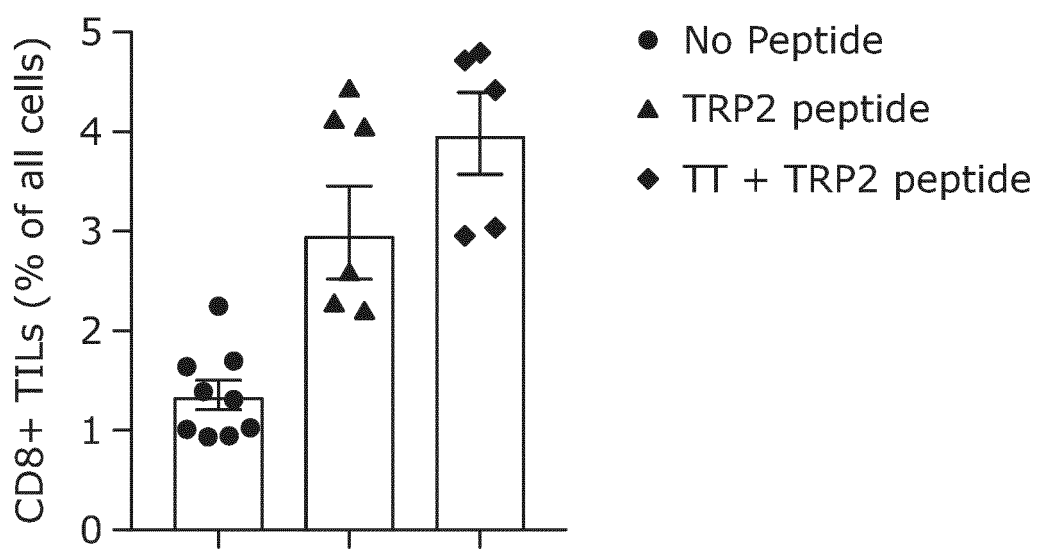

More importantly, inclusion of TT-specific peptides in the cancer nanovaccine resulted in a 75% response rate to anti-PD1, whereas only 28% of mice treated with TRP2-PeptiCRAd and PD-1 blockade experienced a complete tumor eradication (FIG. 4E and FIG. 9A). One of the biggest advantages of combining oncolytic viruses with checkpoint inhibitors is that the viruses in the tumor facilitate and increase the T lymphocyte recruitment, thereby unleashing an unprecedented activity of the monoclonal antibodies. Along this line, we observed a significant increase in CD8+ TILs in mice treated with TT-TRP2-PeptiCRAd in combination with anti-PD-1 (FIG. 4C), when compared to the control treatments (FIG. 4F).

Example 5

Figure 5A:
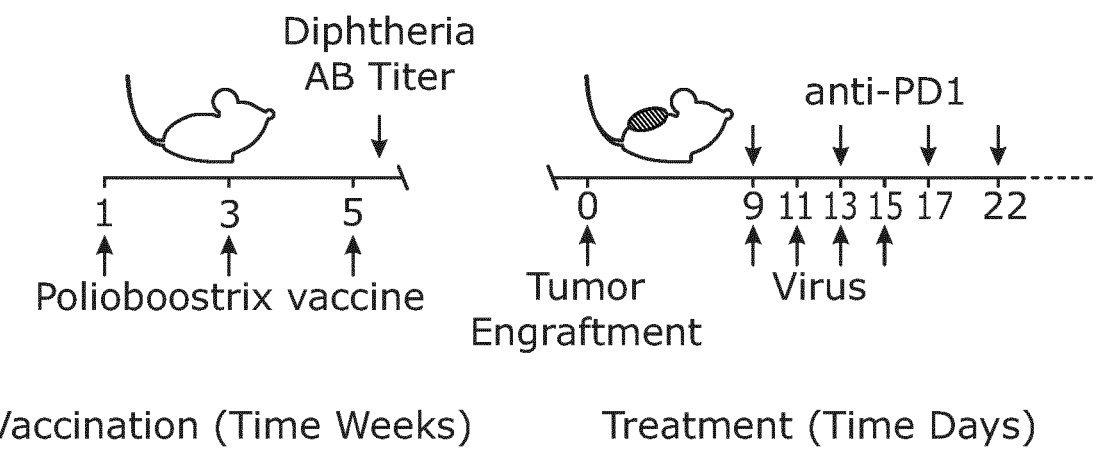
Figure 5B:
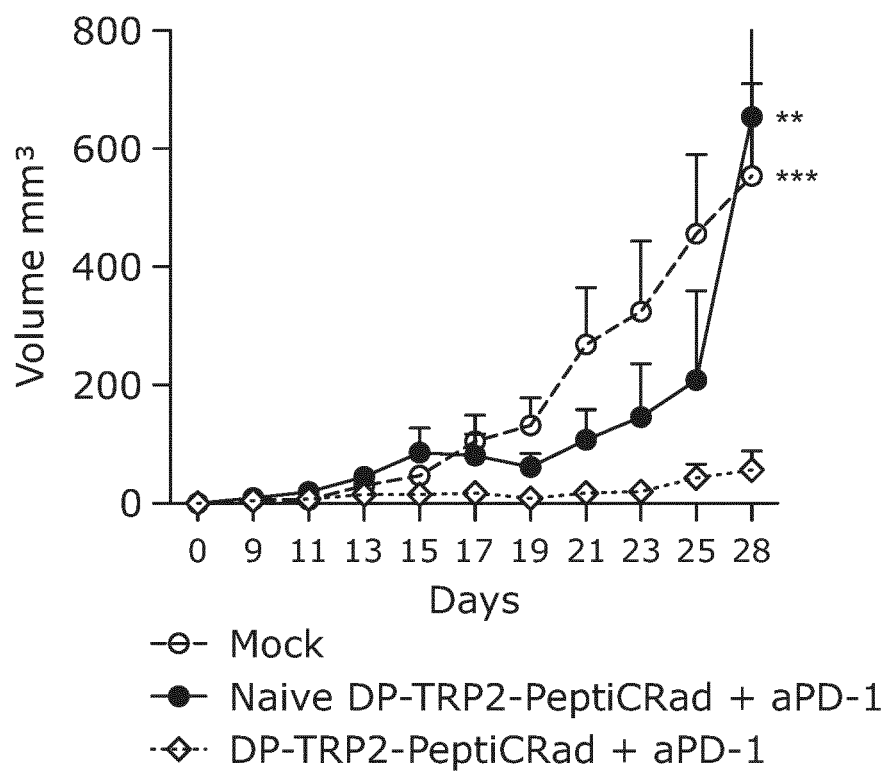

The Pre-Existing Immunity is a General Mechanism to Enhance the Anti-Tumor Response and Reshapes the Immunological Balance in T Cell Repertoire Since we observed that pre-existing immunity to tetanus toxoid potentiates the anti-tumor response of a double-coated PeptiCRAd alone and in combination with PD-1 blockade, we sought to further investigate whether our approach is valid also in the context of a multivalent vaccine such as a tetravalent vaccine. Polioboostrix is a tetravalent vaccine with a high coverage of 85% of infants immunized, making it an attractive study model (25) C57BL/6 mice were pre-immunized with Polioboostrix vaccine with the same immunization regime as before (FIG. 5A). Serum samples and splenocytes were collected and analyzed in order to confirm the effectiveness in the immunization protocol. Tetravalent vaccine was found to efficiently generate both antibodies and CD4+ T cells specific for pertussis and diphtheria (FIG. 10A-C). For the tumor growth analysis, B16.OVA tumors in naïve or pre-immunized mice were treated with anti-PD1 antibodies and PeptiCRAd coated with MHC-II restricted Diphtheria-Pertussis peptides and MHC-I restricted TRP2 peptides (DP-TRP2-PeptiCRAd). Consistent with our previous results, a superior anti-tumor response was detected in pre-immunized treated with DP-TRP2-peptiCRAd and anti-PD1, whereas treatment efficacy was lost in naïve mice (FIG. 5B).

Figure 5C:
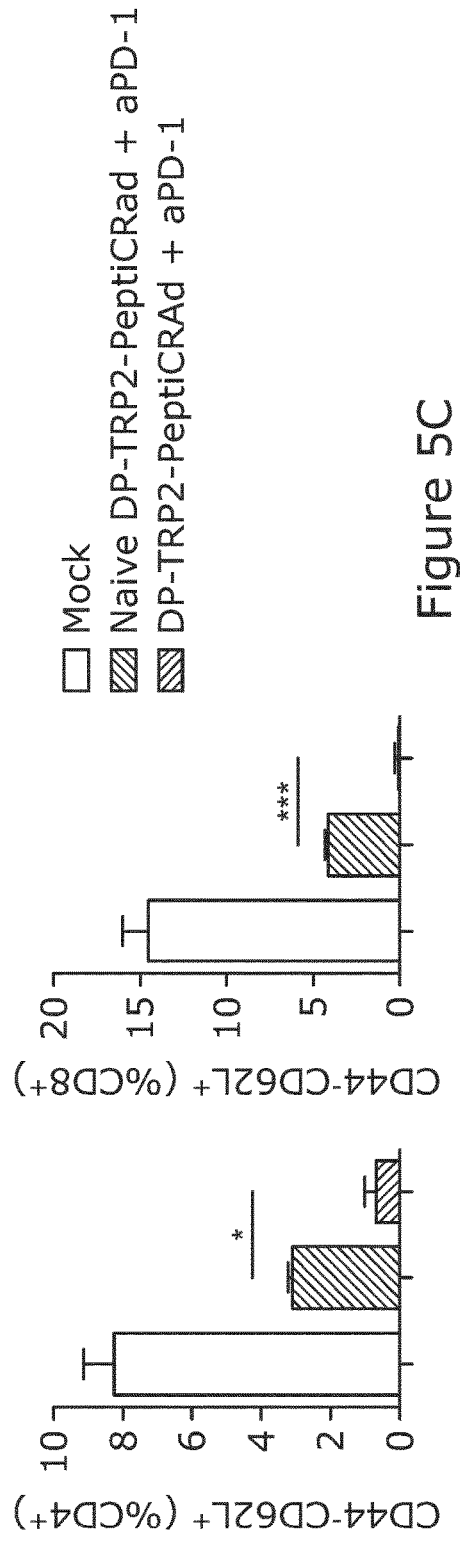
Figure 5D:
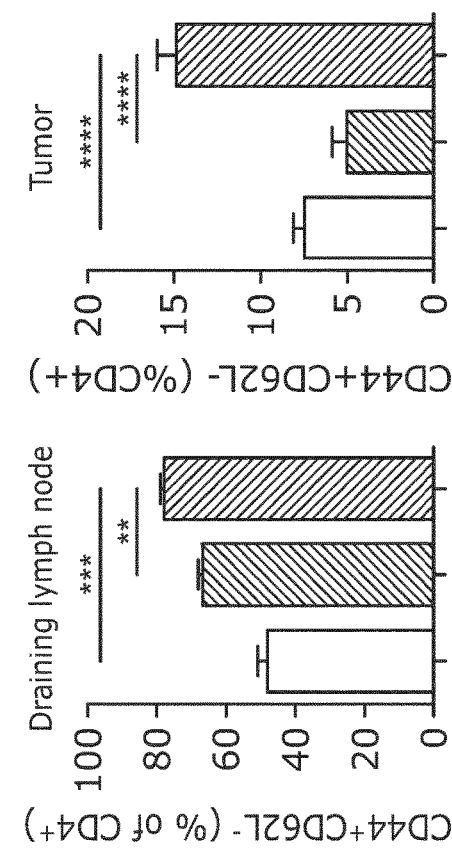

These results confirm that the pathogen-specific pre-existing immunity enhances the anti-tumor response and that the mechanism of action is dependent on the memory T cells. Moreover, this effect is not restricted to tetanus but is adaptable to other pathogens as well. To further verify that the mechanism of action behind the enhanced treatment efficacy using diphtheria and pertussis as the pre-immunizing vaccine, we analyzed the T cell repertoire of the tumor draining lymph nodes, TME and spleen. The frequency of naïve CD8+T and CD4+ T cells was lower in the draining lymph nodes of the pre-immunized, DP-TRP2 PeptiCRAd treated mice compared to the control groups (FIG. 5C). Concomitantly, increased levels of CD4+$T_{EM}$ cells were observed in the draining lymph nodes and in the TME of pre-immunized mice compared to the naïve and mock treated mice (FIG. 5D). In addition, a trend towards higher infiltration of TRP2-specific CD8+ T-cells was seen in the tumour tissue of the immunized mice when compared to the naïve mice (FIG. 10D), and the level of CD4+$T_{EM}$ cells in the tumour and draining lymph nodes strongly correlated with the intensity of the TRP2-specific TIL response. Taken together, the double-coated PeptiCRAd vaccine platform can be used to stimulate pre-acquired, pathogen-specific CD4+ T cell immunity in order to help the generation of effective anti-tumor CD8+ T cell responses.

SUMMARY

Due to the high coverage of international vaccination programs, the majority of the worldwide population has been vaccinated against common pathogens, leading to acquired pathogen-specific immunity with a robust memory T cell repertoire. These vaccines lead to the formation of an immunological memory that is able to deploy a much faster and more effective immune response when re-encountering the pathogen; in fact, the primary immune response is rather weak and slow while the secondary immune response is faster and more effective (26). While CD8+ anti-tumor cytotoxic T lymphocytes (CTL) are the preferred effectors of cancer immunotherapy, CD4+ T cell help is also required for an optimally strong anti-tumor immune response to occur.

Hence, we describe a new cancer immunotherapy approach that takes advantage of the pre-existing pathogen-specific immunological memory present in the worldwide population of vaccinated individuals by investigating whether the pathogen-related CD4+ T cell memory populations could be re-engaged to support the CTLs, converting a weak primary anti-tumor immune response into a stronger secondary one. To this end, we used our PeptiCRAd technology that consists of a virus coated with MHC-I restricted tumor-specific peptides, and developed it further by introducing pathogen specific MHC-II-restricted peptides.

Proof of concept was demonstrated and validated in melanoma using tetanus and polioboostrix vaccines available for humans, highlighting the universal nature of the CD4+ memory in boosting cancer-specific CTL responses. Importantly, the approach can be extended to naturally occurring tumor peptides beyond the surrogate OVA, as well as to other pathogens instead of tetanus, highlighting the usefulness of our technique in taking full advantage of the CD4+ memory T cell repertoires when designing immunotherapeutic treatment regimens.

Finally, the anti-tumor effect was even more prominent when combined with an immune checkpoint inhibitor, such as anti-PD1, strengthening the rationale behind combination therapy with oncolytic viruses.

REFERENCES

8. Ostroumov D, Fekete-Drimusz N, Saborowski M, Kuhnel F, Woller N. CD4 and CD8 T lymphocyte interplay in controlling tumor growth. Cell Mol Life Sci. 2018; 75(4): 689-713.
11. Capasso C, Hirvinen M, Garofalo M, Romaniuk D, Kuryk L, Sarvela T, et al. Oncolytic adenoviruses coated with MHC-I tumor epitopes increase the antitumor immunity and efficacy against melanoma. Oncoimmunology. 2016; 5(4):e1105429.
15. Moore M W, Carbone F R, Bevan M J. Introduction of soluble protein into the class I pathway of antigen processing and presentation. Cell. 1988; 54(6):777-85.
16. Knocke S, Fleischmann-Mundt B, Saborowski M, Manns M P, Kuhnel F, Wirth T C, et al. Tailored Tumor Immunogenicity Reveals Regulation of CD4 and CD8 T Cell Responses against Cancer. Cell Rep. 2016; 17(9): 2234-46.
23. Bloom M B, Perry-Lalley D, Robbins P F, Li Y, el-Gamil M, Rosenberg S A, et al. Identification of tyrosinase-related protein 2 as a tumor rejection antigen for the B16 melanoma. J Exp Med. 1997; 185(3):453-9.
25. Feldstein L R, Mariat S, Gacic-Dobo M, Diallo M S, Conklin L M, Wallace A S. Global Routine Vaccination Coverage, 2016. MMWR Morb Mortal Wkly Rep. 2017; 66(45):1252-5.
26. Laidlaw B J, Craft J E, Kaech S M. The multifaceted role of CD4(+) T cells in CD8(+) T cell memory. Nat Rev Immunol. 2016; 16(2):102-11.

---

The invention claimed is:

1. A viral vector having attached to its viral capsid or envelope, polypeptides that are not genetically encoded by said viral vector but are attached to the capsid or envelope covalently or non-covalently, wherein:
   i) at least one of said polypeptides comprises an antigen from, or of, a pathogen that a subject has been prior immunised against; and
   ii) at least one other of said polypeptides is a tumor or cancer specific polypeptide and so stimulates an anti-tumor or anti-cancer immune response in a subject exposed to said vector.

2. The viral vector according to claim 1, wherein said polypeptides comprise fusion polypeptides, a part of which comprises an antigen from, or of, a pathogen that a subject has been prior immunised against; and another part of which is a tumor or cancer specific polypeptide and so stimulates an anti-tumor or anti-cancer immune response in a subject exposed to said vector.

3. The viral vector according to claim 1, wherein said polypeptides are polylysine-modified or polyarginine-modified for attaching same to said capsid.

4. The viral vector according to claim 1, wherein said polypeptides are attached to the capsid or envelope by a cell penetrating peptide; a cholesterol moiety; or an electrostatic, disulfide or amide bond linkage.

5. The viral vector according to claim 1, wherein said polypeptides are selected from the group consisting of Major Histocompatibility Complex of class I (MHC-I)-restricted polypeptides, Major Histocompatibility Complex of class II (MHC-II)-restricted polypeptides, and DC activating polypeptides.

6. The viral vector according to claim 1, wherein at least one or a plurality of said polypeptides are MHC-I-restricted polypeptides and at least one or a plurality of said polypeptides are MHC-II-restricted polypeptides.

7. The viral vector according to claim 1, wherein said viral vector is a member of a family selected from the group consisting of: Adenoviruses, Reoviruses, Papillomaviruses, Picornaviruses, Caliciviruses, Herpesviruses, Poxviruses, Hepadnaviruses, Flavivirus, Togavirus, Coronavirus, Hepatitis D, Orthomyxovirus, Paramyxovirus, Rhabdovirus, Bunyavirus, Filovirus and Retroviruses.

8. The viral vector according to claim 1 wherein said viral vector is selected from the group comprising: Adenovirus, Herpes Simplex Virus 1 (HSV-1), Herpes Simplex Virus 2 (HSV-2), Vaccinia virus, Vesicular stomatitis Indiana virus (VSV), Measles Virus (MeV), Maraba virus, and Newcastle Disease (NDV) virus.

9. The viral vector according to claim 1, wherein said viral vector is oncolytic.

10. The viral vector according to claim 1, wherein said polypeptide of i) is:

```
                                        (SEQ ID NO: 1)
QYIKANSKFIGITEL (Tetanus toxin);

(SEQ ID NO: 2)
ARYVSQQTRANPNPY (Pertussis);

(SEQ ID NO: 3)
IQSKRFAPLYAVEAK (Polio Mahoney);

(SEQ ID NO: 4)
SPVYVGNGVHANLHV (Diphtheria);

(SEQ ID NO: 5)
PVFAGANYAAWAVNVAQVI (Diphtheria);

(SEQ ID NO: 6)
ARYVSQQTRANPNPY (Pertussis);

(SEQ ID NO: 7)
IQSKRFAPLYAVEAK (Polio Mahoney);
or
                                        (SEQ ID NO: 8)
SPVYVGNGVHANLHV (Diphtheria).
```

11. The viral vector according to claim 1, wherein said polypeptide of ii) is:

```
                                        (SEQ ID NO: 9)
    KVPRNQDWL (gp100);

(SEQ ID NO: 10)
    SLLMWITQC (NY-ESO-1);

(SEQ ID NO: 11)
RGPESRLLEFYLAMPFATPM (NY-ESO-1);

(SEQ ID NO: 12)
    YLAMPFATPMEAELARRSLA (NY-ESO-1);

(SEQ ID NO: 13)
RGPESRLLEFYLAMPFATPMEAELARRSLA (NY-ESO-1;
```

-continued
```
                                        (SEQ ID NO: 14)
PGVLLKEFTVSGNILTIRLTAADHR (NY-ESO-1);

(SEQ ID NO: 15)
YLAMPFATPMEAELARRSLA (NY-ESO-1);

(SEQ ID NO: 16)
YLAMPFATPMEAELARRSLAEE (NY-ESO-1);

(SEQ ID NO: 17)
VFGIELMEVDPIGHLYIFAT (MAGE-A3);
or
                                        (SEQ ID NO: 19)
VFGIELMEVDPIGHLY (MAGE-A3).
```

12. A pharmaceutical composition or immunogenic agent or vaccine comprising said viral vector according to claim 1 and a suitable carrier.

13. An isolated target cell comprising said viral vector according to claim 1.

14. A combination therapeutic for the treatment of cancer comprising:
    a) the viral vector according to claim 1; and
    b) a further cancer therapeutic agent.

15. A method of treating cancer in a subject, comprising:
    administering an effective amount of said viral vector according to claim 1 to the subject, thereby treating cancer in the subject.

16. The method according to claim 15 wherein said viral vector is administered in combination with an anti-tumour agent or an anti-seasonal disorder agent.

17. The method of claim 15, wherein said cancer is nasopharyngeal cancer, synovial cancer, hepatocellular cancer, renal cancer, cancer of connective tissues, melanoma, lung cancer, bowel cancer, colon cancer, rectal cancer, colorectal cancer, brain cancer, throat cancer, oral cancer, liver cancer, bone cancer, pancreatic cancer, choriocarcinoma, gastrinoma, pheochromocytoma, prolactinoma, T-cell leukemia/lymphoma, neuroma, von Hippel-Lindau disease, Zollinger-Ellison syndrome, adrenal cancer, anal cancer, bile duct cancer, bladder cancer, ureter cancer, oligodendroglioma, neuroblastoma, meningioma, spinal cord tumor, osteochondroma, chondrosarcoma, Ewing's sarcoma, cancer of unknown primary site, carcinoid, carcinoid of gastrointestinal tract, fibrosarcoma, breast cancer, Paget's disease, cervical cancer, esophagus cancer, gall bladder cancer, head cancer, eye cancer, neck cancer, kidney cancer, Wilms' tumor, Kaposi's sarcoma, prostate cancer, testicular cancer, Hodgkin's disease, non-Hodgkin's lymphoma, skin cancer, mesothelioma, multiple myeloma, ovarian cancer, endocrine pancreatic cancer, glucagonoma, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, acoustic neuroma, mycosis fungoides, insulinoma, carcinoid syndrome, somatostatinoma, gum cancer, heart cancer, lip cancer, meninges cancer, mouth cancer, nerve cancer, palate cancer, parotid gland cancer, peritoneum cancer, pharynx cancer, pleural cancer, salivary gland cancer, tongue cancer or tonsil cancer.

18. A method of treating cancer in a subject, comprising:
    administering an effective amount of the pharmaceutical composition or immunogenic agent or vaccine according to claim 12 to the subject, thereby treating cancer in the subject.

19. A method of treating cancer in a subject, comprising: administering an effective amount of the target cell according to claim 13 to the subject, thereby treating cancer in the subject.

20. A method of treating cancer in a subject, comprising: administering an effective amount of the combination therapeutic according to claim 14 to the subject, thereby treating cancer in the subject.

* * * * *